(12) United States Patent
Stark et al.

(10) Patent No.: US 6,184,797 B1
(45) Date of Patent: *Feb. 6, 2001

(54) COMMUNICATION SYSTEM FOR AN INSTRUMENTED ORTHOPEDIC RESTRAINING DEVICE AND METHOD THEREFOR

(76) Inventors: John G. Stark, 19390 Walden Trail, Deephaven, MN (US) 55391; Shawn B. Dempster, 45 Island Rd., North Oaks, MN (US) 55127

( * ) Notice: Under 35 U.S.C. 154(b), the term of this patent shall be extended for 0 days.

This patent is subject to a terminal disclaimer.

(21) Appl. No.: 09/330,749

(22) Filed: Jun. 11, 1999

Related U.S. Application Data

(63) Continuation of application No. 08/389,680, filed on Feb. 15, 1995, now Pat. No. 5,929,782, which is a continuation-in-part of application No. 08/298,591, filed on Aug. 31, 1994, now Pat. No. 5,484,389, which is a continuation of application No. 07/733,207, filed on Jul. 19, 1991, now Pat. No. 5,368,546, which is a continuation of application No. 07/483,139, filed on Feb. 21, 1990, now Pat. No. 5,052,375.

(51) Int. Cl.[7] .................................................. G08C 19/22
(52) U.S. Cl. ................... 340/870.07; 340/870.01; 340/825.19; 340/517; 340/573; 128/903; 606/102
(58) Field of Search ......................... 340/870.07

(56) References Cited

U.S. PATENT DOCUMENTS

| | | | |
|---|---|---|---|
| 4,952,928 | * 8/1990 | Carroll et al. | 340/825.19 |
| 5,052,379 | * 10/1991 | Ariy et al. | 128/903 |
| 5,153,584 | * 10/1992 | Engira | 340/870.18 |

* cited by examiner

*Primary Examiner*—Michael Horabik
*Assistant Examiner*—Timothy Edwards, Jr.
(74) *Attorney, Agent, or Firm*—Robert A. Elwell

(57) ABSTRACT

A system and method for communicating an orthopedic parameters signal between a remote communication unit and a central site monitoring station is provided. The orthopedic signal includes a value representative of a total torque output by an individual over a period of time as measured by a personal orthopedic restraining device. The restraining device is restrains movement of a first flexibly connected body portion relative to a second body portion. Communication is accomplished by receiving the orthopedic parameters signal at the remote unit from the orthopedic device. Subsequently, the received signal is protected from potential transmission errors through encoding. The encoded signal is prepared for transmission through modulation. Finally, the modulated signal is transmitted over a communication channel from the remote unit to the central station such that movement of flexibly connected body portions can be monitored. In addition, the operations of the central site monitoring station are described.

60 Claims, 15 Drawing Sheets

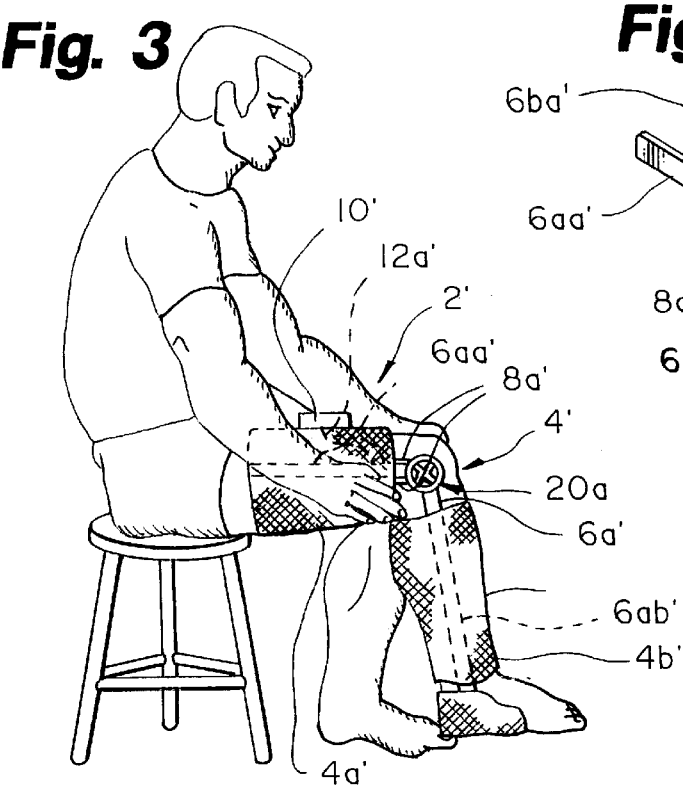
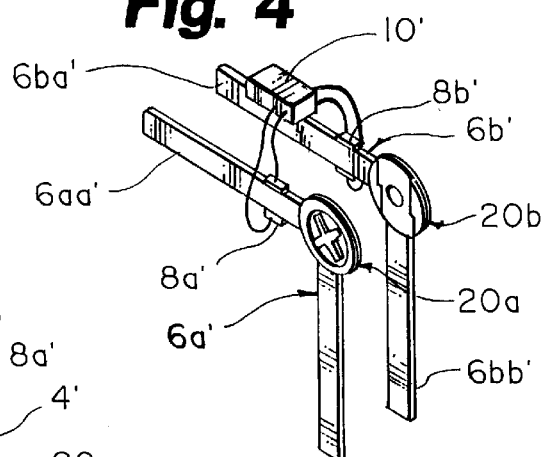
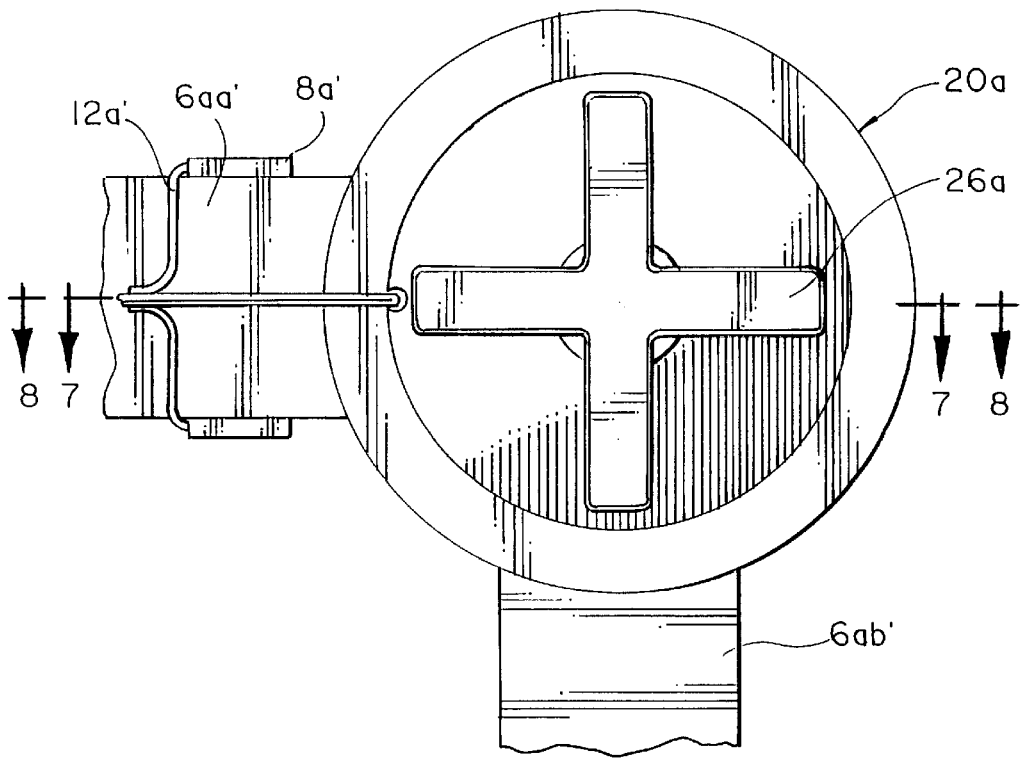

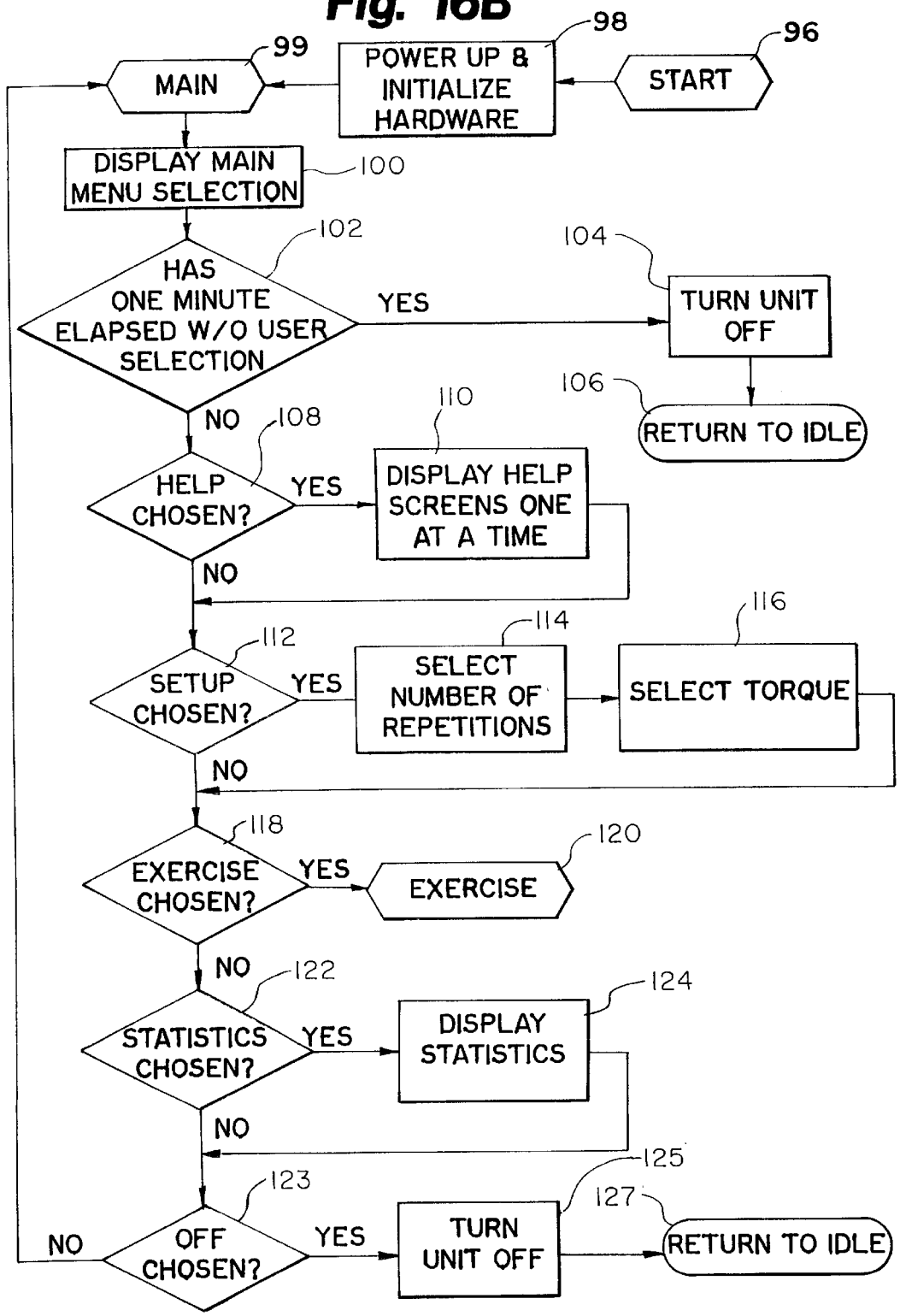

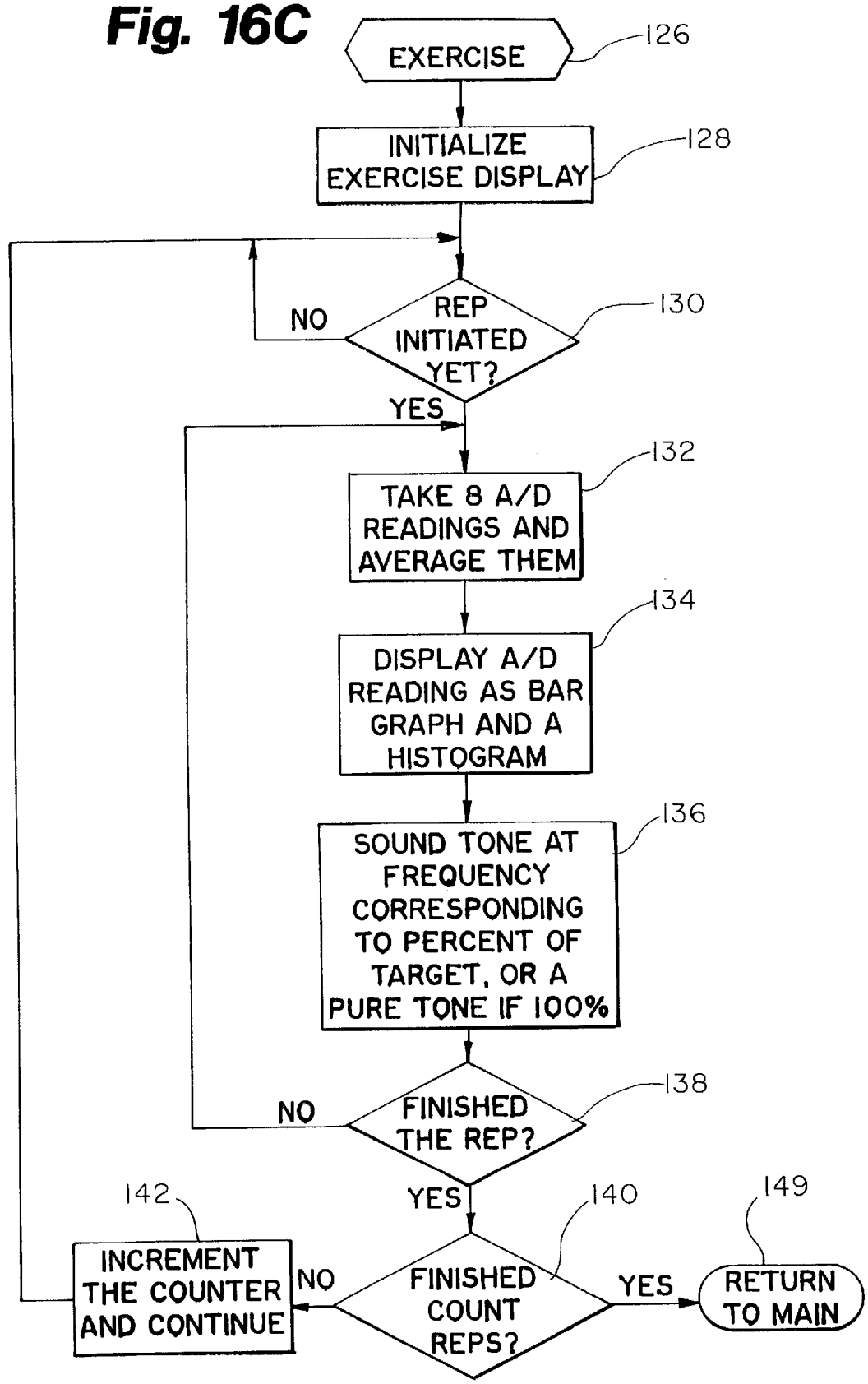

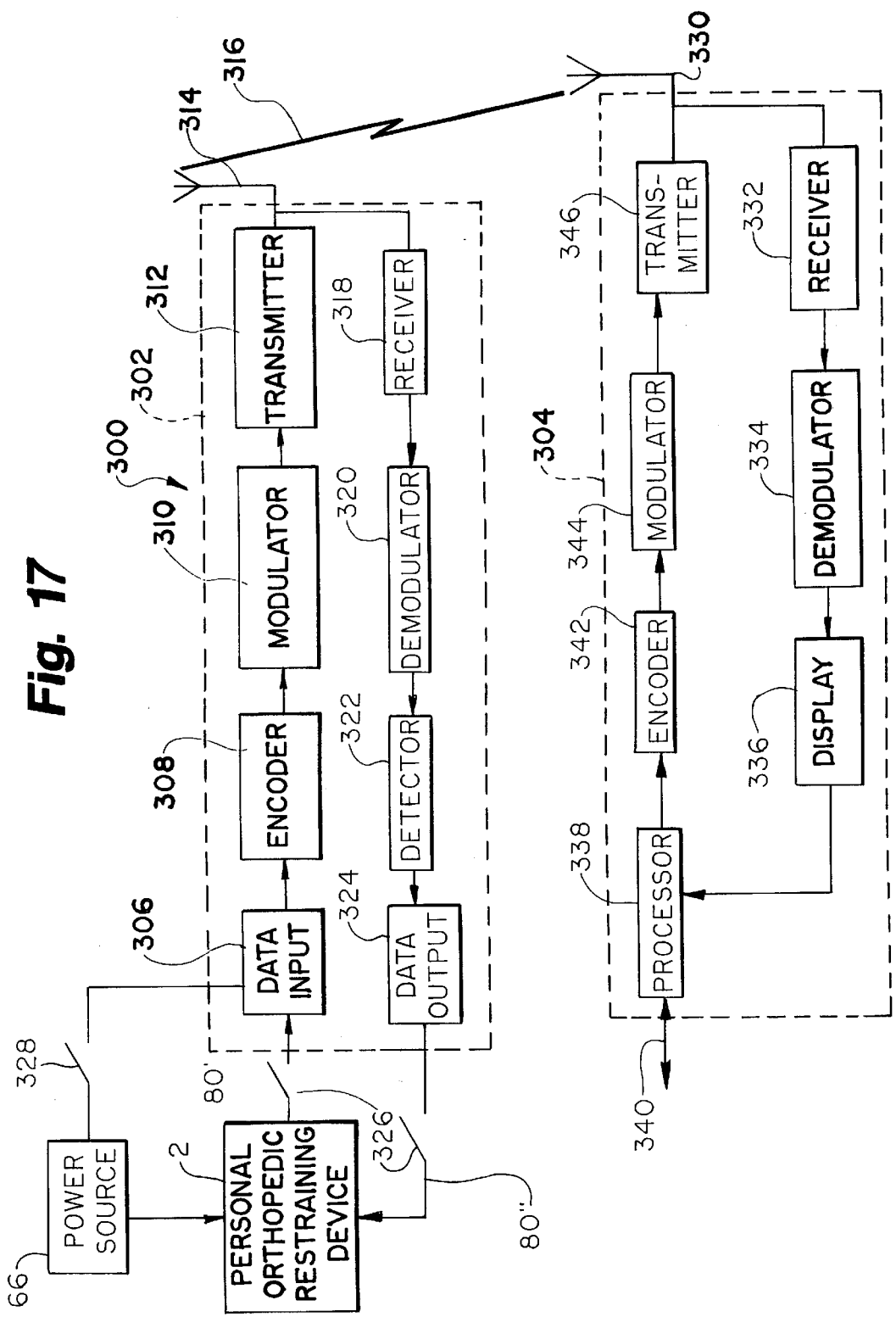

COMMUNICATION SYSTEM FOR AN INSTRUMENTED ORTHOPEDIC RESTRAINING DEVICE AND METHOD THEREFOR

RELATED INVENTIONS

The present invention is a continuation of U.S. patent application Ser. No. 08/389,680 filed Feb. 15, 1995 now U.S. Pat. No. 5,929,782 entitled "Communication System for an Instrumented Orthopedic Restraining Device and Method Therefor" which is a continuation-in-part of U.S. patent application Ser. No. 08/298,591, now U.S. Pat. No. 5,484,389 filed on Aug. 31, 1994, which is entitled "Instrumented Orthopedic Restraining Device And Method Of Use" by Stark et al. which was a continuation of U.S. patent application Ser. No. 07/733,207, now U.S. Pat. No. 5,368,546, filed on Jul. 19, 1991, which is entitled "Instrumented Orthopedic Restraining Device And Method Of Use" by Stark et al. which was a continuation of U.S. patent application Ser. No. 07/483,139, now U.S. Pat. No. 5,052,375, filed on Feb. 21, 1990, which is entitled "Instrumented Orthopedic Restraining Device And Method Of Use" by Stark et al. and which are all assigned to the assignee of the present invention.

FIELD OF THE INVENTION

The present invention relates generally to ambulatory orthopedic restraining devices such as casts, braces and the like. More particularly, the present invention relates to communication of orthopedic parameters from the restraining devices to a central monitoring station.

BACKGROUND OF THE INVENTION

It is known that both muscles and bones should be exercised to maintain strength. It is also known that healing fractures, exposed to permissible weight bearing stress, often heal more predictably and more rapidly than fractures which are not stressed at all. This is probably also true for connective tissues, such as ligaments and articular cartilage.

When an individual sustains a physical injury which involves damage to bones, muscle tissue, connective tissue or the like, the physician treating the individual will make a determination as to whether exercise will be allowed. The physician will allow exercise if the physician can obtain assurances that the exercise will be performed in a controlled manner within specific parameters wherein the injured bone and/or tissue will remain stable. Unfortunately, however, the physician is generally unable to obtain adequate information or assurances about the manner in which a particular patient will conduct prescribed exercise. Furthermore, because the physician is also unable to obtain adequate feedback after the patient performs any specific prescribed exercise, the physician generally does not feel he or she has sufficient access to information about the exercise to permit or recommend anything but the most basic exercise. Without some way to obtain information about exercise events, the physician cannot maintain sufficient control of the exercise. The physician does not know how much stress the patient can or will exert voluntarily, and does not know how well the patient will adhere to a schedule of repetitive exercise events.

Since the physician is not able to obtain adequate feedback regarding the patient's exercise, the most prudent course of action for the physician is to limit the amount of exercise which the patient is allowed to perform by immobilizing the portions of the body proximate the injury. This is often accomplished by using a cast which is the simplest and crudest method of protecting an injury. The cast allows virtually no movement at all and is widely used to insure against reinjuries. Unfortunately, this method of protecting the injury often does not provide adequate means for exercising the body portions proximate the injury. For instance, a cast is often not strong enough, without additional reinforcement, to permit isometric exercising. Furthermore, casts are not equipped to provide feedback to the physician or the patient with respect to any exercising.

Accordingly, a need exists for a personal orthopedic restraining device which will permit and encourage a range of exercise during rehabilitation and provide sufficient feedback to the prescribing physician to allow the physician to evaluate the patient's progress in regard to the exercise the physician has prescribed. A need also exists for a personal retraining device which is equipped to give the patient immediate feedback respecting exercise events. Although it has been known that exercise is helpful in rehabilitating patients and others having orthopedic disabilities, inadequacies, or the like, adequate devices for methods of retraining respective body parts and monitoring the exercise thereof have not been provided which adequately address this problem. This monitoring can be enhanced by utilizing a central monitoring station which receives orthopedic parameters through a communication system.

Communication systems take many forms. In general, the purpose of a communication system is to transmit information-bearing signals from a source, located at one point, to a user destination, located at another point some distance away. A communication system generally consists of three basic components: transmitter, channel, and receiver. The transmitter has the function of processing the message signal into a form suitable for transmission over the channel. This processing of the message signal is referred to as modulation. The function of the channel is to provide a physical connection between the transmitter output and the receiver input. The function of the receiver is to process the received signal so as to produce an estimate of the original message signal. This processing of the received signal is referred to as demodulation.

One type of communication system is a spread-spectrum system. In a spread-spectrum system, a modulation technique is utilized in which a transmitted signal is spread over a wide frequency band within the communication channel. The frequency band is much wider than the minimum bandwidth required to transmit the information being sent. A voice signal, for example, can be sent with amplitude modulation (AM) in a bandwidth only twice that of the information itself. Other forms of modulation, such as low deviation frequency modulation (FM) or single sideband AM, also permit information to be transmitted in a bandwidth comparable to the bandwidth of the information itself. However, in a spread-spectrum system, the modulation of a signal to be transmitted often includes taking a baseband signal (e.g., a voice or data channel) with a bandwidth of only a few kilohertz, and distributing the signal to be transmitted over a frequency band that may be many megahertz wide. This is accomplished by modulating the signal to be transmitted with the information to be sent and with a wideband encoding signal.

Three general types of spread-spectrum communication techniques exist, including direct sequence modulation, frequency and/or time hopping modulation, and chirp modulation. In direct sequence modulation, a carrier signal is modulated by a digital code sequence whose bit rate is much higher than the information signal bandwidth.

Information (i.e., the message signal consisting of voice and/or data) can be embedded in the direct sequence spread-spectrum signal by several methods. One method is to add the information to the spreading code before it is used for spreading modulation. It will be noted that the information being sent must be in a digital form prior to adding it to the spreading code, because the combination of the spreading code and the information typically a binary code involves modulo-2 addition. Alternatively, the information or message signal may be used to modulate a carrier before spreading it.

These direct sequence spread-spectrum communication systems can readily be designed as multiple access communication systems. For example, a spread-spectrum system may be designed as a direct sequence code division multiple access (DS-CDMA) system. In a DS-CDMA system, communication between two communication units is accomplished by spreading each transmitted signal over the frequency band of the communication channel with a unique user spreading code. As a result, transmitted signals are in the same frequency band of the communication channel and are separated only by unique user spreading codes. These unique user spreading codes preferably are orthogonal to one another such that the cross-correlation between the spreading codes is low (i.e., approximately zero).

Particular transmitted signals can be retrieved from the communication channel by despreading a signal representative of the sum of signals in the communication channel with a user spreading code related to the particular transmitted signal which is to be retrieved from the communication channel. Further, when the user spreading codes are orthogonal to one another, the received signal can be correlated with a particular user spreading code such that only the desired user signal related to the particular spreading code is enhanced while the other signals for all of the other users are de-emphasized.

It will be appreciated by those skilled in the art that several different spreading codes exist which can be used to separate data signals from one another in a DS-CDMA communication system. These spreading codes include but are not limited to pseudonoise (PN) codes and Walsh codes. A Walsh code corresponds to a single row or column of the Hadamard matrix.

Further it will be appreciated by those skilled in the art that spreading codes can be used to channel code data signals. The data signals are channel coded to improve performance of the communication system by enabling transmitted signals to better withstand the effects of various channel impairments, such as noise, fading, and jamming. Typically, channel coding reduces the probability of bit error, and/or reduces the required signal to noise ratio (usually expressed as bit energy per noise density (i.e., $E_b/N_0$) which is defined as the ratio of energy per information-bit to noise-spectral density), to recover the signal at the cost of expending more bandwidth than would otherwise be necessary to transmit the data signal. For example, Walsh codes can be used to channel code a data signal prior to modulation of the data signal for subsequent transmission. Similarly PN spreading codes can be used to channel code a data signal.

It will be appreciated by those skilled in the art that the use of these spread-spectrum signals in a communication system is highly desirable, because under current federal communications commission (FCC) rules no license is required to operate such devices if particular frequencies are used.

The present invention provides a solution to these and other problems, and offers other advantages over the prior art.

SUMMARY OF THE INVENTION

The present invention provides a communication system for an instrumented orthopedic restraining device (e.g., a brace). This communication system transfers therapeutic information (e.g., an orthopedic parameters signal) between a patient wearing a brace and a doctor or technician who is monitoring the healing progress of the patient from a remote location.

In accordance with a first aspect of the invention, a communication unit is provided. The communication unit includes a data input which receives an orthopedic parameters signal representative of a sensed stress in a personal orthopedic restraining device. The sensed stress preferably is a value representative of a total torque output by the individual over a period of time as measured by the personal orthopedic restraining device. The restraining device is designed to restrain movement of a first flexibly connected body portion relative to a second flexibly connected body portion of an individual who is wearing the restraining device. An encoder is operatively coupled to the data input to protect the received orthopedic parameters signal from potential transmission errors by encoding the received orthopedic parameters signal. A modulator is operatively coupled to the encoder to prepare the encoded orthopedic parameters signal for subsequent transmission by modulating the encoded orthopedic parameters signal. Finally, a transmitter is operatively coupled to the modulator to transmit the modulated orthopedic parameters signal over a communication channel such that movement of flexibly connected body portions can be monitored by a central site monitoring station.

The data input preferably includes a mechanism (e.g., buttons, a keypad, touch screen, or the like) for incorporating messages obtained from the individual into the orthopedic parameters signal for transmission to the central site monitoring station. In addition, the orthopedic parameters signal preferably further includes a patient identifier which can be used to identify a particular set of data from a patient at the central station from among several other sets of data pertaining to other patients.

It will be appreciated by those skilled in the art that several encoding techniques exist including interleaving, block coding, convolutional coding, and cyclical redundant coding. In addition, several forms of modulation exist. The encoded orthopedic parameters signal can be modulated according to a communication access type selected from the group consisting of: frequency division multiple access, time division multiple access, and code division multiple access. Also, the communication channel may be one of several types of channels including: an electronic data bus, radio communication link, wireline, optical fiber link, and/or satellite link. The type of communication channel can also be described with reference to a particular channel known in the art. Some of the possible currently existing channels that may be used include a serial port wireline, a parallel port wireline, a public switched telephone network (PSTN), a private data network, a radio data network, a paging channel, a short message service channel, a personal communications service channel, a trunked radio channel, a cellular radio channel, and/or a satellite link.

The communication unit also includes a detachable connection mechanism for selectively connecting the communication unit to the personal orthopedic restraining device. This will allow the patient to attach the communication unit only when needed as well as provide for easy replacement of the communication unit should it need repair or maintenance. The communication unit also has a power supply (e.g., a rechargeable battery) which is detachably connected to the personal orthopedic restraining device and the communication unit. The power supply preferably is shaped and arranged for optimal positioning on the individual which will be wearing the personal orthopedic restraining device and the communication unit.

In some instances, it may be necessary for the individual wearing the restraining device to get a message from the central station or for the communication unit/restraining device to receive instructions from the central station. Therefore, the communication unit is also configured with a receiver for receiving a communication from the central site monitoring station over the communication channel. The central site monitoring station communication may take many forms including: a message to the individual wearing the personal orthopedic restraining device and the communication unit, a programming instruction for the personal orthopedic restraining device, a request for an orthopedic parameter signal from the personal orthopedic restraining device, a request to resend a portion of an orthopedic parameter signal previously sent by the personal orthopedic restraining device, and/or confirmation that a previous orthopedic parameter signal was received. As a result of some of these communications, the communication unit may need to provide the central site monitoring station communication to the personal orthopedic restraining device and has a data output provided for such purposes.

In accordance with a second aspect of the invention, a central site monitoring station communication unit is provided. The central site monitoring station communication unit includes a receiver for receiving a modulated orthopedic parameters signal from a personal orthopedic restraining device worn by an individual. The modulated orthopedic parameters signal is representative of a sensed stress in the restraining device. A demodulator is operatively coupled to the receiver to demodulate the received modulated orthopedic parameters signal. A detector is operatively coupled to the demodulator to detect an orthopedic parameters signal from demodulated orthopedic parameters signal. Also, data output is operatively coupled to the detector to provide the detected orthopedic parameters signal to an external device such that subsequent processing of the orthopedic parameters signal can be performed.

As previously noted with respect to the communication unit attached to the restraining device, the central site monitoring station communication unit preferably is adapted for use with a variety of different types of communication channels and different modulation schemes. Also, the detector preferably includes a mechanism for detecting transmission errors in the demodulated orthopedic parameters signal. In addition to detecting the errors, the detector preferably includes a mechanism for correcting some types of transmission errors in the demodulated orthopedic parameters signal based on a maximum likelihood sequence estimation algorithm.

The central site monitoring station communication unit also includes a transmitter for transmitting a communication from the central site monitoring station over the communication channel to the personal orthopedic restraining device. This communication, as previously noted, can have several different contents, including: a message to the individual wearing the personal orthopedic restraining device and the communication unit, a programming instruction for the personal orthopedic restraining device, a request for an orthopedic parameter signal from the personal orthopedic restraining device, a request to resend a portion of an orthopedic parameter signal previously sent by the personal orthopedic restraining device, and/or confirmation that a previous orthopedic parameter signal was received.

It may be desirable for subsequent processing to be done to communications received from the personal orthopedic restraining device and as such an external device can be coupled to the central site monitoring station communication unit. The external device preferably processes the orthopedic parameters signal. This orthopedic parameters signal is a sensed stress value representative of a total torque output by the individual over a period of time as measured by the personal orthopedic restraining device. Some of the types of subsequent processing that the external device may perform include: comparing the sensed stress value to an expected value to confirm that the individual's responses are within norms, comparing the sensed stress value to previously received values associated with a patient identifier for the individual to judge the individual's response to treatment, storing the sensed stress value along with previously received values associated with a patient identifier for the individual to create a clinical record, monitoring a prescribed exercise regimen of the individual based on the sensed stress value to monitor compliance with the prescribed exercise regimen, performing statistical analysis of the sensed stress value in conjunction with other values received at the central site monitoring station, providing a message obtained from the individual wearing the personal orthopedic device to another individual at the central site monitoring station, and/or determining a programming instruction to be sent to the personal orthopedic restraining device.

These first and second aspects of the invention also can be implemented in device-implemented methods to communicate an orthopedic parameters signal between a remote communication unit and a central site monitoring station. This communication method includes receiving the orthopedic parameters signal at the remote communication unit from a personal orthopedic restraining device. Subsequently, the received orthopedic parameters signal are protected from potential transmission errors by encoding the received orthopedic parameters signal. The encoded orthopedic parameters signal is prepared for subsequent transmission by modulating the encoded orthopedic parameters signal. Then, the modulated orthopedic parameters signal is transmitted over a communication channel from the remote communication unit and to the central site monitoring station such that movement of flexibly connected body portions can be monitored by the central site monitoring station.

The device-implemented method also preferably includes storing two or more different orthopedic parameters signals before transmitting any signals such that modulated versions of the stored two or more orthopedic parameters signals are transmitted in a single transmission burst over the communication channel. This storing technique can be used to reduce the overall power consumption of a communication unit by reducing the average number of transmissions that a communication unit performs in a given time period.

The device-implemented method may consist of only a one-way communication scheme in which case several provisions about the operation of the communication unit must be made. For example, the receiving component in the communication unit may be limited to only activate after a particular action has occurred. These actions may be a prescribed exercise regimen having been completed, a periodic reporting time having occurred, at least two different orthopedic parameters signals having been generated by the personal orthopedic device, and/or a message having been obtained from the individual for incorporation into the orthopedic parameters signal for transmission to the central site monitoring station.

Alternatively, the device-implemented method may include receiving a communication from the central site monitoring station over the communication channel such that a two-way communication scheme is performed. Once again, the receiving component in the communication unit may be limited to only activate after a particular action has occurred. These actions may include: a prescribed exercise regimen having been completed, a periodic reporting time having occurred, at least two different orthopedic parameters signals having been generated by the personal orthopedic device, a message having been obtained from the individual for incorporation into the orthopedic parameters signal for transmission to the central site monitoring station, and/or a communication having been received from the central site monitoring station which requests an orthopedic parameter signal from the personal orthopedic restraining device. If a communication is received from the central site monitoring station, then the communication preferably is provided to the personal orthopedic restraining device.

In the two-way communication scheme a limited-short or a full-long communication may be received from the central site monitoring station. The two types of communications may be distinguished by the amount of information contained in the message. Several communication channels currently have or are planning to have provisions for providing limited-short messages which are less expensive and more available than channels capable of full-long messages. Either type of message can be sent on a variety of channels including: a radio data network, a paging channel, a short message service channel, a personal communications service channel, a trunked radio channel, a cellular radio channel, and/or a satellite link. The limited-short communication which has a small information content may include: a request for an orthopedic parameter signal from the personal orthopedic restraining device, a request to resend a portion of an orthopedic parameter signal previously sent by the personal orthopedic restraining device, and confirmation that a previous orthopedic parameter signal was received. In contrast, a full-long communication may be any of those mentioned for the limited-short communication as well as a message to the individual wearing the personal orthopedic restraining device and the communication unit and/or a programming instruction for the personal orthopedic restraining device.

These and various other features as well as advantages which characterize the present invention will be apparent upon reading of the following detailed description and review of the associated drawings.

BRIEF DESCRIPTION OF THE DRAWINGS

FIG. 3 is a side view of an alternative orthopedic restraining device in accordance with the present invention.

FIG. 4 is a schematic illustration of the orthopedic restraining device show in FIG. 3 showing elongated restraining bars located on either side of the device.

FIG. 5 is an enlarged side view of an incrementally adjustable hinge shown in FIG. 3.

FIGS. 16A through 16C are functional flow diagrams of control logic for an orthopedic device in accordance with the principles of the present invention.

FIG. 17 is a block diagram showing a preferred embodiment communication system in accordance with the present invention.

DETAILED DESCRIPTION OF THE PREFERRED EMBODIMENT

Figure 1:
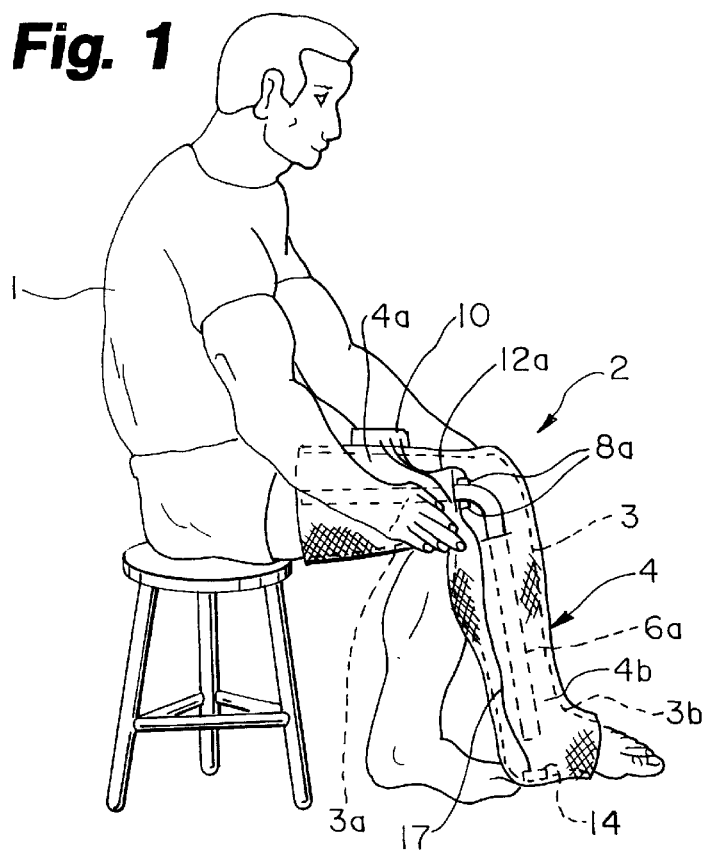
FIG. 1 is a side view of an orthopedic restraining device in accordance with the present invention.

Prior to describing the preferred embodiments of the present inventions, the following background material is provided as a further foundation to support an understanding of the advantages the present invention offers over the prior art.

The process of strengthening the extremities is an essential element in orthopedic and rehabilitation treatment. Many patients suffering from joint, ligament, or muscle damage or disease could function better if they had adequate motor power to control the damaged or diseased tissue. Strengthening the damaged or diseased extremity, when it can be achieved, is a safe and normally effective way of improving function. Therefore, treating physicians generally resort to strengthening quite early in the treatment process.

Strengthening is not always achieved, however. Failure to strengthen the extremity may occur because of poor patient understanding, lack of motivation or pain. It may also result because of the apparent contradiction between the need to protect the damaged or diseased tissue from further trauma and the need for exercise.

In order to provide for improved strengthening procedures, the orthopedic and physical therapy communities need an improved means to control the damaged or diseased extremity while:

1. Encouraging strengthening through feedback.
2. Controlling the strengthening by monitoring.
3. Storing the data for subsequent interpretation.

The present device attempts to do this.

Motivational psychology is often enough to prompt a patient to overcome pain when strengthening is necessary. It is, however, not always enough. We are all familiar with the highly motivated athlete who can overcome pain to rehabilitate himself or herself. Few of us think of the severely diseased elderly rheumatoid patient, however, who may be unable to bear any additional amount of pain in an attempt to overcome his or her disease. Psychology works in favor of the athlete because the athlete is a motivated individual. Psychology works against the elderly rheumatoid patient, however, because of depression, anxiety, and fear of pain. The effectiveness of a strengthening program must be measured by its ability to enable the patient to maximize the strengthening which is technically possible in each one of the aforementioned cases.

Strengthening can be optimized by utilizing the technological advances embodied in the present invention. If the exercise program fails for some reason, the data provided by the device will provide an indication of how the exercise program is failing. Patterns of response would indicate the pattern of failure, whether it is motivation, inhibition by pain, lack of commitment or submaximal effort (to name a few possible reasons for failure). The present device attempts to collect and provide objective feedback which can be analyzed by the patient and/or the prescribing physician or therapist. It is really a system. A system of controlling an injured extremity. It will motivate the individual and monitor his or her progress for safety and efficiency. It may also have significant applications for uninjured individuals as well.

The advantages of the present device over prior devices include:

1. Its sophistication.
2. Its complex relationship of several otherwise unrelated principles of physiology and engineering.
3. Its recording and documentation abilities.
4. Its ability to motivate and remind the individual.

Strengthening programs using isometric means have been demonstrated in the past to have important predictable affects on strengthening. However, the programs have generally been executed in isolation by the patient. The conventional physical therapy programs often work because of the intense coaching and supportive environment which the physical therapy setting provides. This involves extraordinary expenses, however, just to overcome motivational and psychological factors. Theoretically, many of the modalities provided in the therapist's office could be administered at home if the patient could obtain enough emotional support, control, and motivation by other means.

The present device will enhance the patient's ability to receive the support, control and motivation needed for an effective program of treatment. Because the device is fairly sophisticated, some formal training may be necessary for those prescribing its use. The potential need for the device, however, could be tremendous given frequency volume of orthopedic injury and disease.

The strengthening of muscle has become a science. There are many methods available, and among those methods, there are various proponents of specific techniques and various attitudes about timing, magnitude of stress, overall training periods and the like.

The isometric method which is the method primarily employed by present invention, has advantages and some disadvantages. It should not be suggested as a replacement for all other types of strengthening. Strengthening effects are often very specific to individual conditioning or individual body structure. Instead, the isometric method should be considered an adjunct or, in certain cases, the only possible method in light of the particular damage, disease or other changes.

There are basically three different methods for muscle strengthening. They are: first, isotonic, second, isokinetic, and, third, isometric.

Isotonic literally means same weight or same resistance. The best example of an isotonic exercise is the body builder with free weights. Basically when the body builder picks up a 100 pound weight, it weights 100 pounds through the entire range of motion. It weighs 100 pounds regardless of whether or not the individual can generate 100 pounds of resistance to move it. If there is injury or pain, there is no way to relieve the body of that 100 pound weight. The muscle and body complex must, through injury or pain, either drop the weight risking further injury, or set it down under control, again risking further injury and pain.

How can a simple 100 pound free weight cause an individual to risk injury? The common individual has little difficulty exerting 100, 200 or more pounds of force in a squat or on certain types of resistive machines. An example of such a resistive machine is the so-called knee bench. An individual sitting on the bench is asked to extend the knee against resistance, usually that resistance is provided through a cable, sling or bracket which fits across the leg and is mechanically connected to the weight. Through an attempt at knee extension, the weight moves up and down against gravity. The problem with this type of device results when the knee becomes painful or cartilage damage results. If cartilage damage or pain results of 45 degrees flexion, the patient must still relax the knee another 45 degrees down to 90 degrees of flexion before the weight and stresses are relieved. It is this movement under stress or pain which enables proponents of isokinetic knee exercise equipment to have a great issue. It is one of the arguments used to advocate isokinetic exercise.

The term isokinetic literally means "same motion". The person exerting against an isokinetic machine exerts a maximal amount, whatever that amount is, and the machine provides only that identical amount of resistance. For example, if a delicate female, in pain, can only exert 10 pound of resistance to straighten the knee, the attached machine will provide only 10 pounds of resistance. This is under the control of the professional administrating the treatment. Returning to the example of the football player, running down the field moves the knee at a specific angular rate which approximates 300 degrees per second. (The knee is moving from flexion to extension and back). Isokinetic proponents argue that training should therefore occur at 300 degrees per second and that the best possible training will occur if the patient is trained to exert his maximal force at a rate, not a fixed resistance.

This relates to the specificity philosophy of training. Specificity training means that training should most accurately reproduce that which will be exerted on the playing field.

These are valid arguments and are highly appropriate to the otherwise healthy knee requiring a maximum amount of strengthening. Isokinetic exercise does not interfere or compete with isometric exercise.

There are patients, however, who cannot exercise against an isokinetic machine, the knee hurts too much, the damaged surfaces are too painful, or the rapid motion of the knee against resistance under load results in further damage.

Isometric literally means "same length". The muscle is held at a fixed length and required to contract. This is the basis of the quadriceps setting exercise, the least stressful form of knee exercise and the exercise of last resort in the painful knee. A foundation of orthopedic treatment in the painful knee is to prescribe straight leg raising exercises. This is to avoid the risk of further damage and to avoid problems with equipment or transportation. One problem with isometric exercise is the muscle is exercised without motion and at one particular length, and the patient will probably derive a minimum amount of benefit for those dynamic activities of daily living requiring strength through a range of motion or at other muscle lengths. Examples of such activities include climbing stairs, running down a football field, stepping off a curb, and a variety of pivoting, twisting activities.

For those individuals where isokinetic exercise is inappropriate, the prescription of isometric exercise has included a variety of modifications, most of which are unsophisticated. We may ask each individual to lock one foot against the other and hold in it at a fixed degree while forcing the legs in opposition. This provides no control, no feedback, and no assurance that it is being done to a maximum extent. Also it is fairly laborious and boring.

We may ask the individual to plant his foot beneath a fixed object, such as a sofa or another chair, and ask him or her to attempt to lift the object without any form of fixation. The patient generally flexes or extends the joint, and the movement which results can cause further pain and damage, resulting in a failure of the exercise program.

We may ask the individual to report to the physical therapy department and use an isokinetic machine fixed at certain points of flexion. This gives a certain amount of readout, flexibility and feedback, but it is generally very expensive. It cannot generally be accomplished any more frequently than once or twice a day and must, because of time and expense, be self-limited. The patient must hopefully derive some personal benefit from this exercise method so that, when the time and expense dictate, it can be discontinued and the patient can go on to additional strengthening by other methods. After such a program, the patient may maintain some permanent benefits (which is unlikely) or deteriorate in function over time because of the limitations of availability. Often the ultimate result is that the patient is at the same level as before therapy started.

How can this data be interpreted and modified for the Patient's benefit? Knapik et al (1983. The Journal of Orthopedic And Sports Physical Therapy 5:58–65) did an interesting study where he compared various forms of exercise including isometric exercise, isotonic exercise and isokinetic exercise. (Isokinetic exercises were done at various rates of movement). The information gained bears directly upon the problems outlined in this chapter. Knapik et al found the following:

1. Maximum torque is possible with isometric exercise.

2. Individuals vary in their torque curves (maximum torque over various degrees of flexion) and that these torque curves may be further modified by injury of disease.

3. "Isometric curves are valid reflections of isokinetic curves."

4. The individuals own torque curve should be studied as reflective of injury, disease, disability and the pattern of needed rehabilitation.

5. Isometric curves best represent the maximal voluntary capability of the muscle group.

There is a tremendous volume of literature data relating to the three basic types of muscle strengthening. The conclusions seem valid and applicable to the isometric conditioning device.

First of all, patients can generate their maximum torque with an isometric exercise. This is useful in that it suggest the patient's maximum ability to exercise is reflected by isometric exercise. For a patient who can barely generate any type of extension force, least of all against an isokinetic machine, the form of exercise which maximizes their abilities would be most useful.

The force curves through the range of motion do vary from individual to individual. This is a reflection of the patient's own mechanics, body make-up, muscle physiology and three dimensional joint anatomy. There are also a myriad of other factors. Knapik's paper suggests that the force curves should be measured and that isometric exercise is a valid way to measure them. The ambulatory personal orthopedic restraining device, or isometric conditioning device (ICD) of the present invention may, therefore, because of its portability, individuality and methods of reinforcement, be the best method of maximizing the rehabilitation program.

Because the isometric curve is an accurate reflection of the isokinetic curve, the use of isometric exercise has a direct and important applicability to the function of the diseased extremity. Knapik's study gives excellent credibility to isometric exercise under specific conditions. These conditions include varying the angle at which the exercise is performed.

In summary, isometric, isokinetic and isotonic exercise each have advantages and disadvantages. The strongest advantage associated with isometric exercise is that the injured or diseased extremity can be strengthened in the absence of motion, thereby preferably resulting in less pain and less tissue damage. With appropriate modifications, isometric exercises can be used to obtain results which begin to approximate the results generally obtained with isokinetic exercises in certain situations when isokinetic exercises are not possible. The fact that program modifications enable one to obtain some of the benefits of isokinetic exercise from isometric exercise is of critical importance to the usefulness of the present device.

The articulations of the human body, commonly called joints, are not simple structures. Each is a complex combination of mechanical alignment, and biophysical properties under the control of muscles which are of themselves, dynamic structures.

Joints are usually characterized in some simplistic fashion such as ball and socket, hinge, fixed, or the like. Ball and socket joints probably resemble the structures after which they are named, more than most other structures do. Hinge joints, on the other hand, vary greatly in their structure, mechanics and dynamic action, and possess only the more general characteristics of a simple hinge for which they are named.

Probably the "simplest" hinge joint would be the elbow. The two condyles of the elbow share nearly the same center of rotation. The condyles themselves are nearly circular when viewed laterally and the opposing surface, the olecranon (of the forearm, ulna), is nearly circular as well. This by itself simplifies the mechanics of joint understanding a great deal. Its simplicity, on the other hand, reflects the complexity of other joints, such as the knee.

Joints, being living structures, and being designed very specifically for appropriate measures of mechanical advantage, stress, weight distribution, rotational stability, and the like impose demands upon professionals who would seek to assist them to recover from injury and disease.

A hydraulic cylinder under pressure exhibits the same pressure near the end of its excursion as it does at its beginning. This is because the cylinder is uniform. The piston is unchanging. The mechanical effect of the hydraulic fluid is defined by that piston size, and as long as it is uniform, the mechanical effect is the same.

The muscle on the other hand is quite different. Muscle cannot extend an infinite distance. It works efficiently within a fairly narrow range between 0.7 and 1.2 times its resting length. It rapidly loses efficiency at either extreme. It's greatest efficiency is at a slight degree of lengthening beyond its resting length.

If one combines what is known about the elbow, arguably the simplest of the hinge joints, with the complexity of physiologic muscle which changes its efficiency over distance, one begins to understand the complexity of what is a simple joint/muscle construct.

If one now combines the complexity of muscle efficiency with a very complex joint, such as the knee, further complexities result. The knee is not a simple hinge joint, but is actually a cam working against a fairly flat surface. As the knee goes into flexion, the degree of excursion of the tendon increases. The pulley, across which the quadriceps tendon works, is not a simple round mechanical device, which is entirely uniform, but it is a rocking, pivoting, sliding structure, which is thicker in some areas than in others, and which exerts pressure through a greater surface area in some degrees of motion than in others. The patella is articulating with a cam-like surface, which is at a different point of flexion and relative prominence than the tibia, which is bearing against the femur in a different area. Finally, there is an element of rotation, because the two cam-like surfaces of the knee are not identically shaped. One is smaller, shorter and rounder than the other, causing the knee to "rotate out of the way" in flexion.

In effect then, what we have here are variables working upon variables. The muscle may be gaining efficiency because it is being stretched from its resting length but the mechanical advantage of its tendon may be gained or lost because of patellofemoral anatomy, rotation of the tibia or other change of normal joint physiology.

If one further compounds abnormal joint physiology with the inhibitory effects of a pain reflex, apprehension or poor cooperation, the problem can be fully appreciated.

The present invention provides a device which can be used to address the difficulties inherent in this set of variables. Because it is basically, a measuring, monitoring, and controlling device, the present device can, with proper use, minimize pain, control the extremity and measure output, strength, and cooperation.

The present device would be able to measure the individual strength curve for that particular subject and individual. The strength curve would likely fit, or fail to fit, a pattern as defined by research in the field. The interplay between the relative factors of muscle length and joint anatomy would be removed as they currently complicate isotonic and isokinetic types of exercise.

Removal of translational forces. If an individual has disruption of the joint surface, the normal translation of one surface over the other is disrupted. Such surfaces commonly can handle compressive loads fairly well, but the increased abrasion which occurs with translation of disrupted surfaces may further damage those symptoms or at a minimum aggravate the patient's symptoms. The discomfort which results from such translation through a spinal reflex may cause interference with the patient's voluntary attempts at exercise. It may cause involuntary interferences as well. Finally, in a patient with emotional factors of anxiety or failure of understanding, the interplay between the volitional, involuntary, psychological factors becomes a morass which obscures the process of strengthening.

In summary, some patients simply must have every possible advantage in order to benefit from a strengthening program. Some patients have the normal psychological make-up, strong need to recover and virtually any type of exercise program (or perhaps no exercise program at all) will be satisfactory to their needs. To those patients where such positive factors are not present, the negative factors must be addressed one by one, individually removing physiologic blocks to recovery (such as reflex inhibition), anatomic blocks to recovery (such as joint irregularity), pain (such as might be experienced with attempts to move a recently operated joint), or failure of understanding (which with a sophisticated device, could not only instruct, but also record and reinforce for the patient).

At the current time, orthopedists as prescribing professionals for individuals with knee problems, often recommend straight leg raising exercises and quadriceps setting exercises for patients. The recommendation is often fairly nonspecific and based upon what the physician interprets the convenience of the patient to be. Quadriceps setting exercises are ordinarily performed with the patient sitting, the knee is usually fully extended and the patient is asked to forcefully contract their muscle, attempting to straighten it further. This ordinarily is demonstrated by some movement of the patella and a highlighting of the outline of the quadriceps and other muscles of the thigh. Straight leg raising exercises are usually performed with the patient supine on the floor. The patient is asked to raise his leg straight up, approximately 12 inches and allow it to rest again. Both exercises are done repetitively. The rationale behind these exercises is that they require the muscles to contract under minimal restriction, in a protected position *(full extension) and since this requires no motion, it is generally accepted as being nonstressful and comfortable. Little has been recognized about the relative merits of these two different types of exercise as they apply to the specific muscles which require strengthening.

Gough and Ladley (1971, Physiotherapy 57:356–361) noticed that quadriceps contraction was greater with isometric exercises (quadriceps contraction was greater with isometric exercises (quadriceps setting) than straight leg raising exercises.

Skuja et al. (1980, Physical Therapy 60:582) noted more activity in the vasti with isometric exercises as opposed to straight leg raising. Soderberg and Cook (1983 Physical Therapy 63:1434–1438), noted that only the rectus femoris was more active in straight leg raising exercises than during quadriceps setting exercises (isometric exercises).

Stratford 1981, Physical Therapy (62:279–283) noticed decreased electromyographic activity at 0 in knees with effusions than at 30, suggesting that slight tension of the muscles is important in the injured knee. Krebs et al. (1983, Arch Phys Med Rehabil 64:441–447) suggested highly significant position dependent effects of exercise in healthy and postarthrotomy knees.

Soderberg et al. (1987, Physical Therapy 67:1691–1696) seem to confirm the conclusions of Soderberg and Cook (1983, Physical Therapy 63:1434–1438) when they demonstrated that quadriceps setting exercises seemed to selectively result in more contraction of the rectus femoris muscle in a great majority of patients.

Haberichter et al. (1985. Physical Therapy 65:723) noted that slight pressure on the muscles seemed to have an effect on increased contractual force.

The summary of the above referenced articles suggests that: (A) quadriceps setting exercises are a separate and distinct type of exercise from straight leg raising exercises and have important effects on the majority of muscles about the knee (the basti, the biceps and the gluteus): (B) that there is a position dependent effect of exercise in the injured knee; and (C) that modifications in patient's exercise program should be aimed specifically at maximizing the known effects of these two different types of exercise by: (1) applying slight tension and performing the exercises in flexion; (2) applying slight compression to the muscle; and/or (3) performing both straight leg raising exercises and isometric exercises.

These findings highlight the importance of control as it applies to an otherwise rather simple exercise without a restraining device. The quadriceps setting isometric exercise is extremely difficult to perform in a position other than full extension. The literature suggests that a change in position is important in the injured knee with effusion. Other literature suggests that multiple positions are important for maximal strengthening in knees with other types of problems.

This literature, particularly the article by Stratford, has led the applicants to believe that casts should be applied with the knee in slight flexion for physiological reasons. It is further suggested that contraction of the quadriceps muscle inside the cast may serve an important need at that fixed degree of flexion. A monitoring and controlling device, such as the present instrumented cast or brace, would therefore be very helpful.

Other inferences are also suggested by the literature. Most important among these is the inference that isometric exercise is separate and distinct from the straight leg raising exercise. In the applicants' opinion, it is difficult to instruct a patient in isometric quadriceps setting contraction because the patient will see no movement. Instructions to the patient to observe the knee cap or observe the contour of the quadriceps muscle are often met with a lack of understanding. This response often leaves the physician with questions as to: (A) whether or not the exercises will be performed (without a firm conviction of their significance, method and importance; and (B) if they are performed in the best possible manner, whether a monitoring and control device should be used to assist the patient to do this.

If the patient derives benefit from a straight leg raising exercise as an isolated exercise, which benefits the rectus femoris, then there is no reason why they could not do this exercise with an embodiment of the present device in place, thereby deriving the benefit of whatever weight and resistance the device could provide. The preferred embodiment of the present invention is obviously not intended for isolated strengthening of the rectus femoris if in fact, the rectus femoris is most well strengthened by straight leg raising.

However, questions are raised by the literature. These exercises, because of the limitations of prior art equipment, are all performed with the knee in extension or near full extension. It may be that once the knee is flexed, the straight leg raising exercise is no longer the best possible exercise for the rectus femoris. In addition, nothing is said about the wave form of the muscle contractions in any of these exercises. There is essentially no control over this aspect of the degree of isometric contraction. It would seem that slight contractions gradually building to a maximum crescendo, and then tapering off under voluntary control, may be a more elegant and more effective to perform isometric contractions.

Since the biceps (which is an antagonist of the quadriceps muscle) and the gluteus (which is related only peripherally and proximally) both demonstrate EMG activity other questions arise.

For instance, what is the effect on these muscles at various points of flexion. Something about the patient's individual coordination may cause these muscles to fire as agonists or antagonists at various other points of flexion of the knee. Obtaining the dees are a separate effects is yet another advantage of the present invention. Muscles other than those obviously contracting and those obviously being protected by the device are being recruited. This suggests that the patient is getting a more general form of strengthening and conditioning by doing an isometric exercise. Therefore, anything which could encourage and monitor the isometric exercise program would benefit the patient more generally by affecting many muscles. In view of the foregoing, it will be appreciated that the advantages of isometric exercises will be enhanced through the use of the present invention.

In the next section, "Angular Specificity" is discussed. "Angular specificity" means the following: strength gains obtained with exercise, usually isometric exercise at one point of flexion, are associated with strength gains at adjacent points of flexion. Usually strength gains at those adjacent points of flexion are proportional to their proximity to the isolated point of flexion where the exercises are performed.

For example, if one does isometric exercise at 50 degrees of knee flexion, and one attempts to extend the knee beyond this point against infinite resistance, strength gains will be measurable at that point of flexion over time. In other words, the patient will be able to exert a greater force after regular exercise in 2 to 4 weeks. These strength gains will continue to increase within physiological limits as time passes. What is suggested in the literature is that similar strength gains will be measurable at points of flexion surrounding that 60 degree point so that the patient will be stronger also at 55 degrees, at 50 degrees, at 40 degrees. Literature data leads us to believe that this effect is measurable and fairly reliable in relatively small groups of study at points within 20 degrees of the point of maximal exercise. Some authors have suggested strength improvements well beyond that angle of exercise. Some have suggested strength improvements at 45 degrees from the angle of exercise. These strength improvements are more difficult to demonstrate, because a higher number of test subjects seem to be required. Statistics, individual variations, joint anatomy, and other factors come into play Knapik et al. (1983, The Journal Of Orthopedic And Sports Physical Therapy 5:58–65, Lindh, 1979, Scand J. Rehab Med 11:33–36). Knap et al (1983, The Journal of Orthopedic And Sports Physical Therapy 5:58–65). Knapik (1983) exercised two groups of individuals; one by isometric means at 90 degrees of flexion, the other by isokinetic means between 45 and 135 degrees of flexion. He then measured both groups isometrically. He found out that isometrically gained strength at 70 degrees and 110 degrees was measurable and statistically comparable with the gain obtained at 90 degrees. He concluded that there was transfer of strength gain (angular specificity) within 20 degrees at the angle of the original exercise. Other literature suggests similar findings, that angular specificity is present, and that angular specificity, if overlapping, because of multiple points of exercise, may help the patient regain strength through the entire range of movement. It will be appreciated, therefore, that the isometric exercise routines of the present invention will greatly enhance the overall strength gains of the patient utilizing a device of the present invention.

Figure 2:
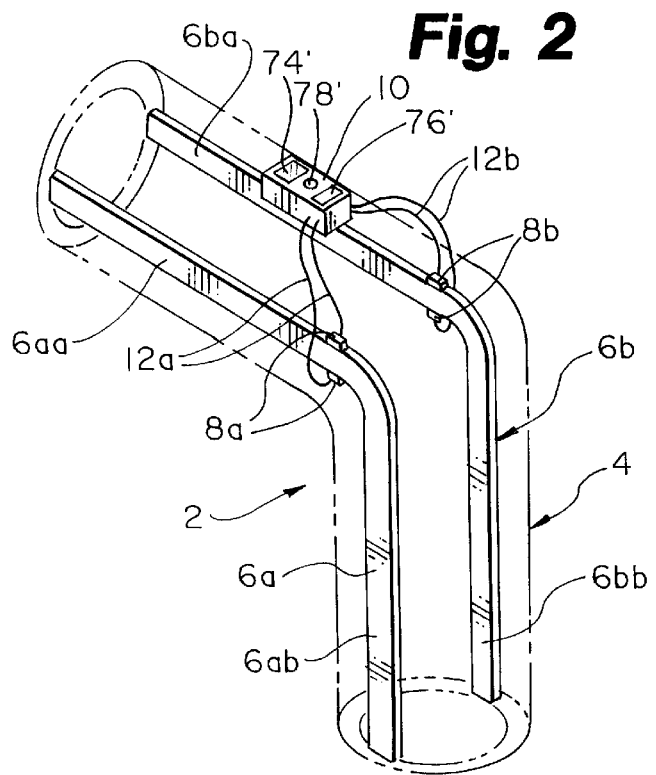
FIG. 2 is a schematic illustration of the orthopedic restraining device show in FIG. 1 showing elongated restraining bars located on either side of the device.

Referring now to the drawings, and to FIGS. 1–2 in particular, a personal orthopedic restraining device 2 in accordance with the present invention is illustrated when engaged with upper and lower leg portions of a right leg 3 of an individual 1. The restraining device 2 includes a housing 4. The housing includes first and second distal end portions 4a and 4b which are configured to receive upper and lower leg portions 3a and 3b of the individual's right leg 3 which are flexibly connected at the knee. The housing 4 further includes a pair of elongated restraining bars 6a and 6b disposed on opposite sides of the individuals right leg 3. Each of the elongated restraining bars 6a and 6b have first and second distal end sections 6aa and 6ba, and 6ab and 6bg, respectively. Each of the distal end sections is fixedly secured to the respective end portion of the housing proximate thereto. Attached to opposite edges of each of the elongated restraining bars 6a and 6b are separate strain gauges 8a and 8b respectively. In preferred embodiments the strain gauges 8a and 8b are foil type strain gauges, each consisting of two strain gauges such that each elongated bar member 6a and 6b are equipped with four strain gauges which are interconnected in a wheatstone bridge circuit arrangement to provide superior sensing capabilities. The strain gauges are capable of sensing stress on the elongated restraining bars and provide an output which is indicative of a quantitative stress level. The strain gauges 8 are electrically interconnected with a programmed microprocessor control unit 10 which includes a mechanism for indicating a quantitative stress value based upon an output from the strain gauges 8 which sense stress on the respective elongated bar members 6a and 6b to which the individual strain gauges are attached. The device 2 also includes a pressure sensing mechanism or load cell 14 which senses pressure placed on the cell 13 when the individual places eight on the leg 3. The load cell 14 is interconnected by a wire 17 with the control unit 10 which can monitor and record outputs from the load cell 14.

An isometric restraining device 2 in accordance with the present invention includes a restraining mechanism 4 including an elongated restraining bar 6a, two strain gauges 8a attached to the restraining bar 6a, and a control unit 10, including a stress indicating mechanism, interconnected to the strain gauges 8a by interconnecting wires 12a. The restraining device 2 also includes a second elongated restraining bar 6b proximate the inside of the subject's leg in FIG. 1. The other restraining bar 6b also equipped with two strain gauges 8b which are attached to the bar and electrically interconnected to the control unit 10 in a similar manner to that shown in FIG. 1. Both restraining bars 6a and 6b are shown in FIG. 2.

Now referring also to FIGS. 3 and 4, the present invention also provides an alternate personal orthopedic restraining device 2 including elements corresponding to those of the previously described restraining device 2. In addition, however, each of the elongated restraining bars 6a' and 6b' include an incrementally adjustable hinge 20a or 20b interconnecting the respective distal end sections 6aa' and 6ab'; or 6ba' and 6bb'. The fist and second distal end portions 4a' and 4b' of the housing 4' are interconnected by the elongated restraining bars 6a' and 6b' which are fixedly secured thereto. The respective first distal end sections 6aa' and 6ba' are fixedly secured to the first distal end portion 4a' and the second distal end sections 6ab' and 6bb' (not shown) are fixedly secured to the second distal end portion 4b' so that these elements of the alternate restraining device 2' move as though they were separate portions of an integral unit. The plurality of strain gauges 8a' and 8b', respectively, are attached to the elongated restraining bars 6a' and 6b'. These strain gauges 8a' and 8b' are electrically interconnected with a control unit 10'.

It will be appreciated that the present invention may be made with a single strain gauge attached to a single elongated bar. However, it is preferable to include an elongated bar on either side of a point of flexion such as a knee, an elbow or the like. Similarly, it is preferable to include at least two strain gauges 8 on each of the elongated bars 6 and, preferably, four strain gauges in an unbalanced whetstone bridge circuit arrangement or configuration.

Figure 6:
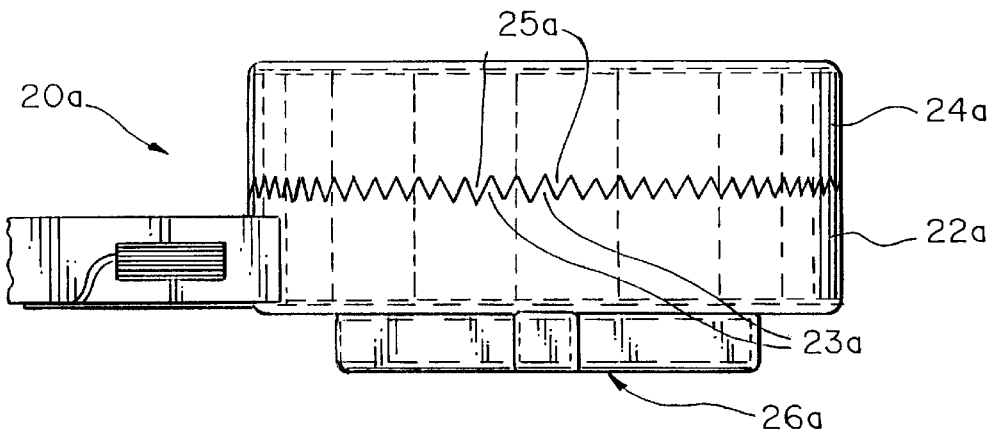
FIG. 6 is a top view of the adjustable hinge shown in FIG. 3 when its respective engaging members are engaged.
Figure 7:
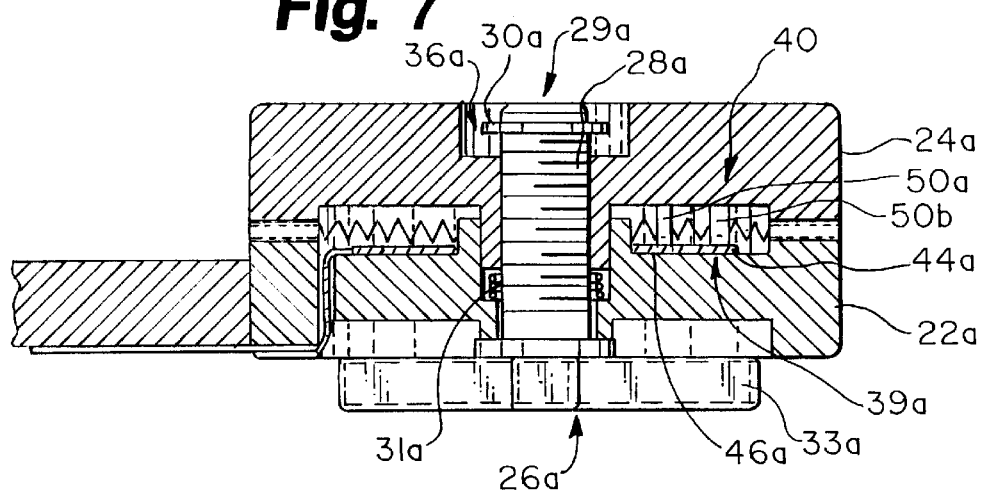
FIG. 7 is a sectional view of the adjustable hinge from the line 7—7 of FIG. 5 when the respective engaging members are engaged.
Figure 8:
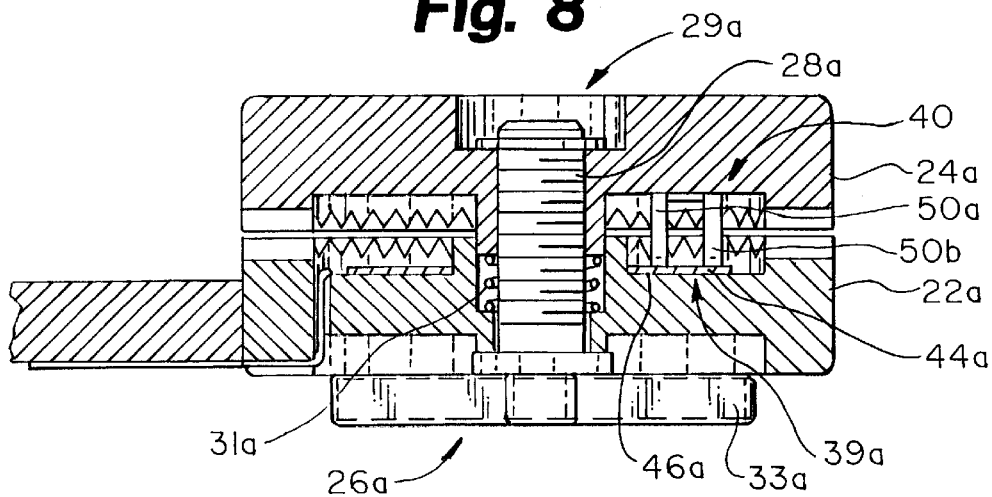
FIG. 8 is a sectional view of the adjustable hinge from the line 8—8 of FIG. 5 when the respective engaging members are disengaged.

Referring now also to FIGS. 5–10, the adjustable hinge apparatus 20a includes a first engaging member 22a which is engageable with a second engaging member 24a. The first engaging member 22a is interconnected with the first distal end section 6aa of the elongated restraining bar 6a and the second engaging member 24a is interconnected with the second distal end section 6ab of the elongated restraining bar 6a. Each of the respective engaging members include engaging teeth, 23a and 25a respectively, which engage one another in a reciprocal relationship when the respective engaging members 22a and 24a are tightened or screwed together as shown in FIGS. 6 and 7. When the respective engaging members 22a and 24a are not tightened together, as shown in FIG. 8, they are free to turn or pivot with respect to one another on a bolt portion 28a of a securing member 26a which is retained within a bolt receiving opening 29a in the second engaging member 24a. The bolt receiving opening 29a is located in the circumferential center of the second engaging member 24a so that the bolt portion 29a of the securing member 26a provides an axial pivot point for the respective engaging members 22 and 24a, with respect to one another, when they are not secured together.

The bolt portion 28a of the securing member 26a is retained in the bolt receiving opening 29a be a retaining clip 30a which is attached to the bolt portion 28a such that the bolt portion 28a cannot be removed from the bolt receiving opening 29a. This prevents the securing member 26a from becoming entirely disengaged from the second engaging member 24a when the securing member 26a is unscrewed to free the engaging teeth 23a of the first engaging member 22a from the engaging teeth 25a of the second engaging member 24a. When the securing member 26a is unscrewed as far as the retaining clip 30a will allow the bolt portion 28a will bias the first engaging member 22a away from the second engaging member 24a so that the respective engaging teeth 23a and 25a are disengaged and the respective engaging members 22a and 24a can turn or pivot about the bolt portion 28a of the securing member 26a.

The bolt receiving opening 29a of the second engaging member 24a includes a reciprocating screw hole 34a which receives and reciprocates the right-handed screw turns on the bolt portion 28a of the securing member 26a. The bolt receiving opening 29a also includes a recess 36a When the securing member 26a is turned clockwise, the right-handed screw turns of the bolt portion 28a are drawn into the second engaging member 24a by the reciprocating turns of the reciprocating screw hole 34a, and the respective engaging teeth 23a and 25a are gradually drawn closer together. When the securing member 26a is turned as far as it can go in this direction, the coil spring 31a will be tightened together as shown in FIG. 7 and the respective engaging teeth 23a and 25a will be tightened together and engaged such that the respective engaging members 22a and 24a can no longer turn or pivot with respect to one another.

When the engaging members 22a and 24a are tightened together in this manner, as shown in FIGS. 6 and 7, an angle between the respective distal end sections 6aa' and 6ab' of the elongated restraining bar 6a' will be fixed and the device 2' can then be used to restrain an individual wearing or engaged in the device 2' conducting isometric exercises sat a series of different degree of flexion generally corresponding to this angle. This device 2' can also be used to restrain an individual conducting isometric exercises at a series of different degrees of flexion. This can be accomplished by conducting isometric exercises at one degree of flexion when the respective distal end sections 6aa' and 6ab' are set at one particular angle with respect to one another, and subsequently at a second, third, fourth and/or fifth degree of flexion when the respective distal end sections 6aa' and 6ab' are reset at different angles. It will be understood that this will means resetting the angle between the respective end sections of each of the restraining bars 6a' and 6b' in a preferred device 2' which has two restraining bars. This is done by loosening the respective securing members 26a and 26b (not shown) on each side of the device 2', allowing the individual to adjust the flexion of the joint manually, and resecuring the respective engaging members 22a and 24 and 22b and 24b of the respective adjustable hinge apparatus 20a and 20b, such that the respective engaging teeth 23a and 25a and 23a and 25a of both of the adjustable hinges 20a and 20b are fully engaged as shown in FIGS. 6 and 7. When the engaging teeth are fully engaged, and the respective engaging members can no longer pivot with respect to one another, the angle between the respective distal end sections will be fixed and the subsequent isometric exercising can begin.

Preferred embodiments of the present invention also include a control unit 10. The control unit is interconnected with the respective strain gauges and the incrementally adjustable hinges in order that the control unit 10 can receive electrical outputs therefrom. The incrementally adjustable hinge 20a preferably includes a potentiometer-like mechanism 39a which is part of a position sensing device 60 for determining the angle of the respective distal end sections of the respective elongated restraining bar 6 in respect to one another. It will be appreciated that because the angle between respective end sections of respective restraining bars will generally be roughly equivalent, it is not required to have more than one potentiometer mechanism in any device 2'. However, because the elongated restraining bars 6a and 6b of the present device 2' are either similar or identical mirror images of one another, each includes the adjustable hinge apparatus 20a and 20b,respectively, including a potentiometer mechanism 39 which is interconnected with the control unit 10'. Each potentiometer mechanism may have the same elements. Further embodiments of the hinge mechanism may include modification to better approximate the specific anatomic motion of the respective joint partially immobilized or protected by the specific device.

Figure 9:
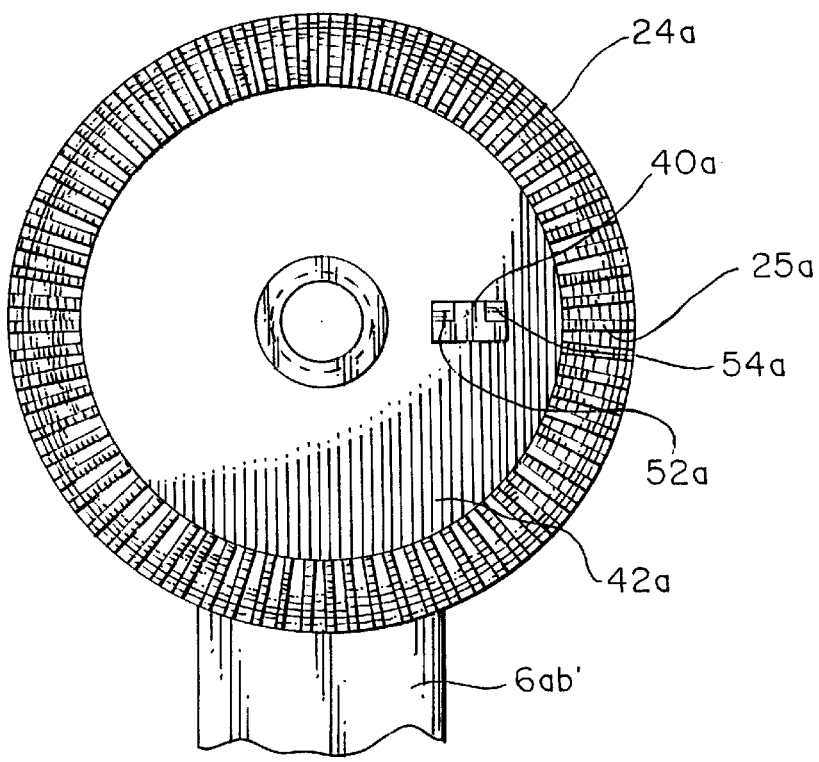
FIG. 9 is a side plan view of a first engaging member of the adjustable hinge shown in FIG. 6.
Figure 10:
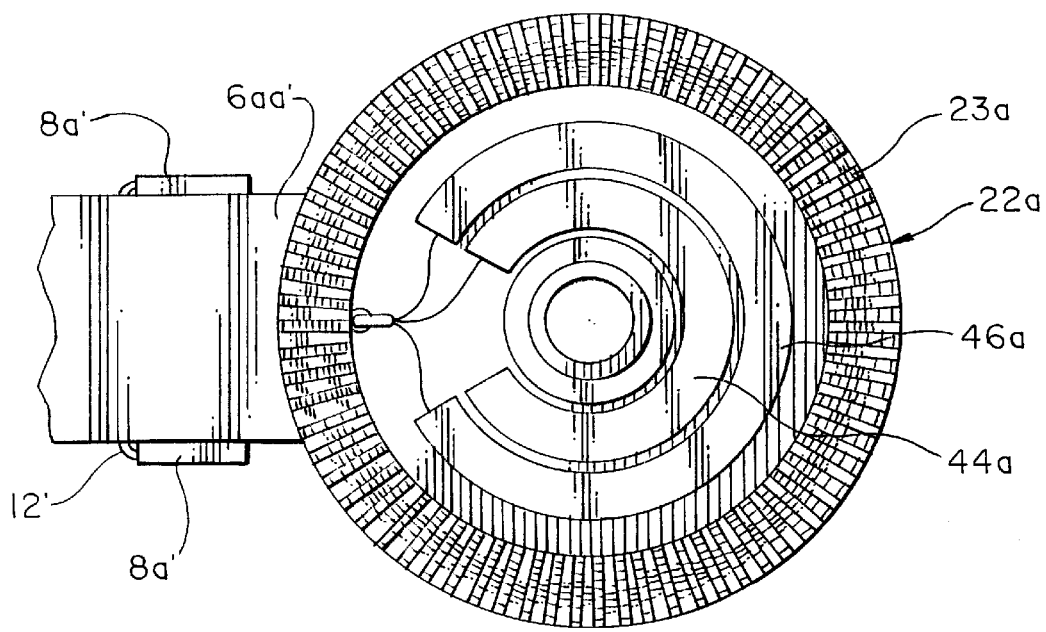
FIG. 10 is a side plan view of a second engaging member of the adjustable hinge shown in FIG. 6.
Figure 11:
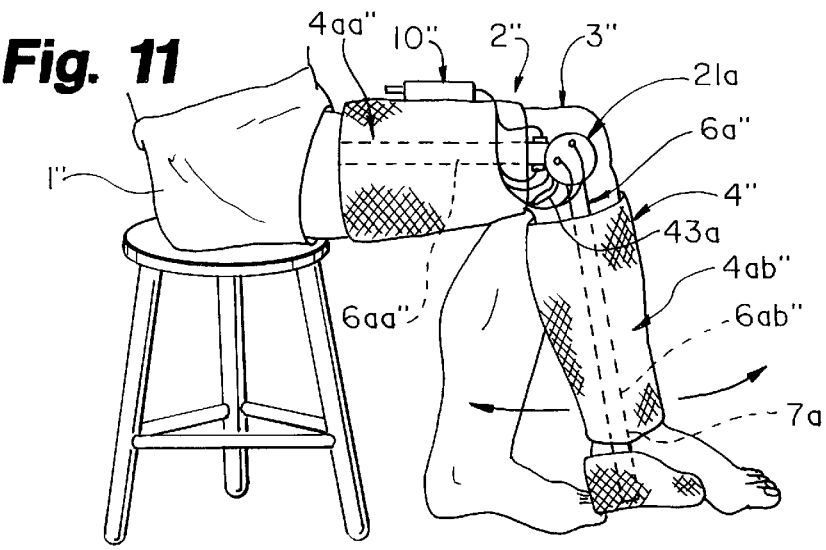
FIG. 11 is a side view of an alternative orthopedic restraining device having an electromechanical hinge.
Figure 12:
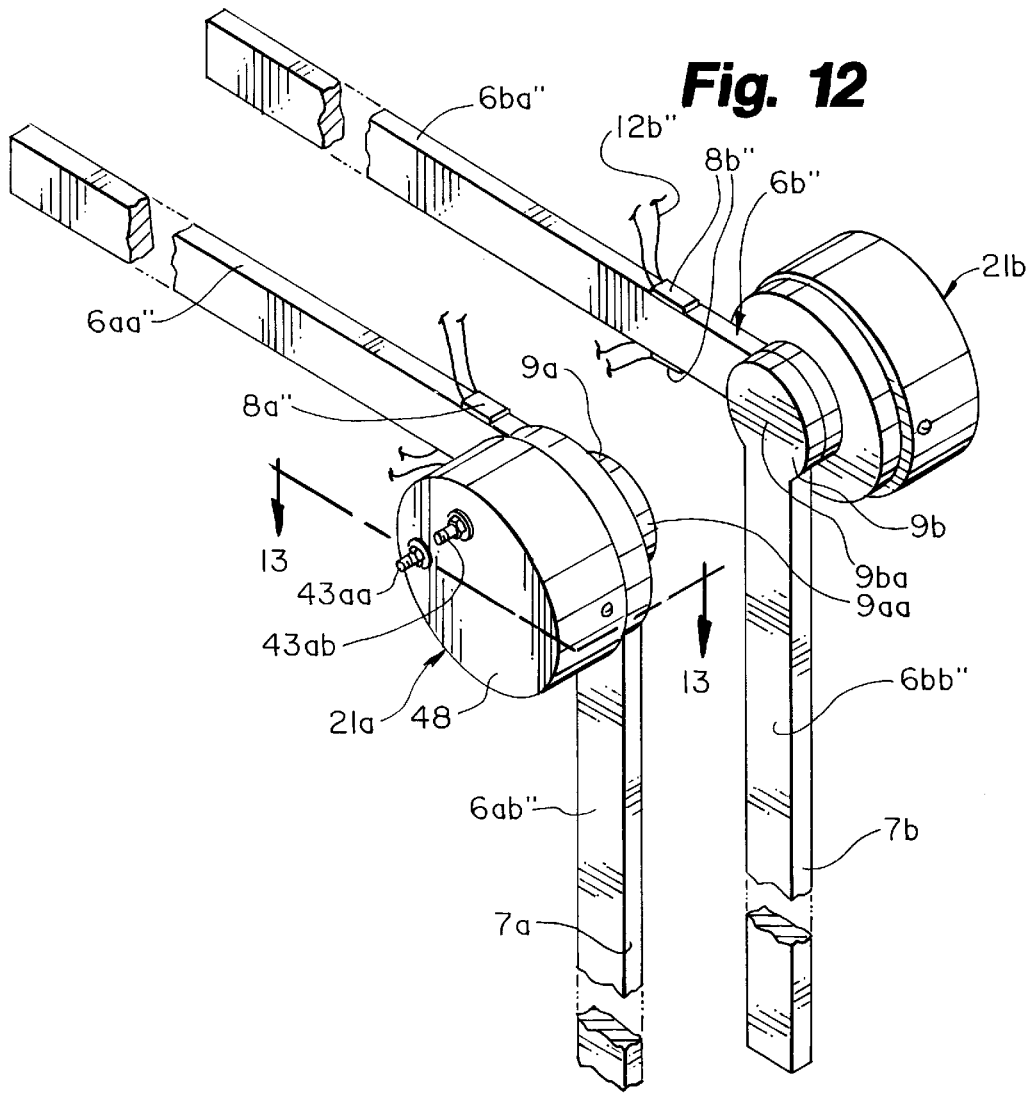
FIG. 12 is a schematic illustration of elements of the alternative orthopedic restraining device shown in FIG. 11.

The potentiometer mechanism 39a shown in FIGS. 7 and 8 incldues a conductive wiper 40a attached or adhered to an inner surface 42a of the second engaging member 24a, a resistive element 44a and a conductive element 46a which are interconnected with the control unit 10' in order that outputs from the potentiometer mechanism 39 can be monitored, and preferably, recorded, by the control unit 10' (See FIGS. 9 and 10 also). The wiper 40a has two resilient contact arms 52a and 54a which extend outwardly from the inner surface 42a of the second engaging member 24a to contact the resistive element 44a and the conductive element 46a, respectively, so that the position of the wiper 40a with respect to the resistive element 44a can be sensed by the control unit 10' reading the electrical output from the potentiometer mechanism 39. In embodiments where there are two hinges only one of the potentiometer mechanisms, if there are two, needs to be interconnected with the control unit 10', although both can be connected. Further, it is recognized that other position sensing means are within the scope of the invention.

Figure 13:
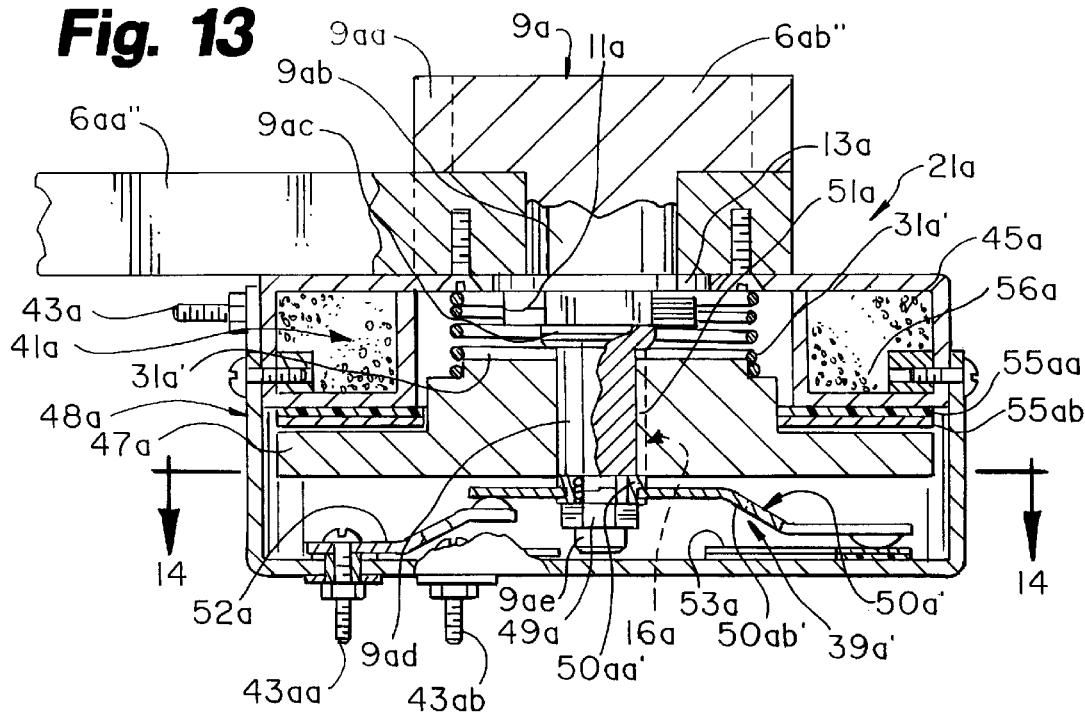
FIG. 13 is a sectional view of the electromechanical hinge shown in FIGS. 11 and 12 from the line 13—13 of FIG. 12.
Figure 14:
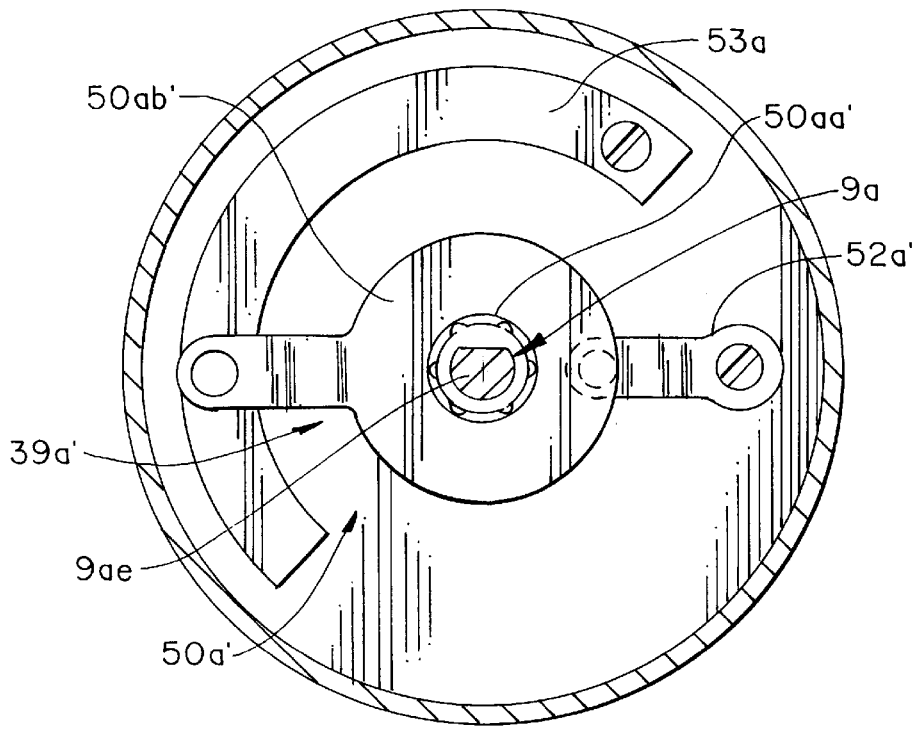
FIG. 14 is a sectional view of the electromechanical hinge of FIGS. 11 and 12 as seen from the line 14—14 of FIG. 13.

Referring now also to FIGS. 11–14, yet another embodiment of the present personal orthopedic restraining device 2" includes a pair of electromechanical hinges 21a and 21b which are incrementally adjustable. This embodiment of the restraining device 2" can include all of the elements of the restraining device 2' shown in FIGS. 3 and 4, except that the incrementally adjustable hinge apparatus 20a and 20b have been replaced by the electromechanical hinge 21a and 21b, which are mirror images of one another. The elements of the electromechanical hinge 21a are shown in FIGS. 13 and 14. The electromechanical hinge 21a is also an incrementally adjustable hinge and includes an alternate potentiometer-like mechanism 39a' which is part of an alternative position sensing device 60' (not shown) for sending an output to a control unit 10", and also includes other elements corresponding to similar elements included in the adjustable hinge apparatus 20a. In the preferred embodiment shown in FIGS. 11–14, the electromechanical hinge 21a is partially controlled by the control unit 10".

The electromechanical hinge 21a includes an electromechanical brake and/or clutch mechanism 41a similar to those which are standard in the art. The preferred electromechanical clutch mechanism 41a is interconnected with the control unit 10" by lead wires extending from leads 43a which are electrically interconnected with a stator coil 45a within a stator housing 56a which is designed to attract a magnetically attractable armature 47a when a sufficient magnetic field is created by an electric current passing through the stator coil 45a. The current is derived from a source of electricity within the control unit 10". Separate lead wires connect the potentiometer-like mechanism 39a' of the position sensing device 60' (not shown) to the control unit 10' so that the electrical output, which provides an indication of the angle between the respective distal end sections 6aa' and 6ab', can be monitored and/or recorded by the control unit 10".

The electromechanical hinge 21a shown in FIGS. 11–14 includes a clutch housing 48a which is secured to the first distal end section 6aa" or 6ba" of the respective elongated restraining bar 6a'. A similar hinge 21b is incorporated into the other restraining bar 6b'. In FIG. 13, a cross-sectional view of the electromechanical hinge 21a is interconnected to the elongated restraining bar 6a" is shown. The second end section 6ab" is an integral unit including an extended restraining bar segment 7a and a shouldered pin or bolt segment 9a. The shouldered pin segment 9a includes a plurality of pin portions 9aa, 9ab 9ac, 9ad and 9ae. The first pin portion 9aa is integrally connected to the proximate end of the extended restraining bar segment 7a. Together with the second pin portion 9ab, the first pin portion 9aa defines a first shoulder upon which the first distal end section 6aa" can rest as it turns about the second pin portion 9ab when the respective distal end sections are allowed to pivot with respect to one another by the electromechanical hinge 21a.

The third pin portion 9*ac* has a threaded exterior for receiving a nut 11*a* for securing the first distal end section 6*aa*" to the second distal end section 6*ab*" over the shouldered pin segment 9*a*. The nut 11*a* secures a washer 13 against the first distal end section 6*aa*", such that the first distal end section 6*aa*" can turn freely about the second pin portion 9*ab* when it is permitted to turn by the electromechanical brake/clutch. The fourth pin portion 9*ad* is received by an opening (not shown) in the magnetically attractable armature 47*a*. The armature 47*a* includes a spline 51*a* which fits into an armature groove 16*a* for receiving the spline 51*a*, located in the fourth pin portion 9*ad*, so that the armature 47*a* will only turn in a common rotary movement with the shouldered pin segment 9*a*. The fourth pin portion 9*ad* and the fifth pin portion 9*ae* define a fourth shoulder against which a wiper arm 50*a*' is secured. The fifth pin portion 9*ae* includes a threaded exterior for receiving a second nut 49*a* which secures the wiper arm 50*a*' against the fourth shoulder. The fifth pin portion 9*ae* also includes a flat side which provides a key to turn a molded insulating element portion 50*aa*' of the wiper arm 50*a*' which is bonded to the conductive element 50*ab*' thereof. The insulating element 50*aa*' is made of a suitable polymeric material which insulates the shouldered pin segment 9*a* from the electrical current which normally flows through the conductive element 50*ab*' of the wiper arm 50*a*'. This is essential to the integrity of the potentiometer circuit. Because the wiper arm 50*a*' is keyed to the fifth pin portion 9*ae*, it will turn in a common rotary movement with the entire shoulder pin segment 9*a*. As the wiper arm 50*a*' turns, it remains in contact with a contact arm 52*a*' which is connected to one of the leads 43*aa* which is in turn electrically interconnected with the control unit 10". The other lead 43*ab* is interconnected with a resistive slide line element 53*a* and also with the control unit 10". The potentiometer-like mechanism 39*a*' is electrically interconnected with the control unit 10" to provide an output to the control unit 10" which can be calibrated to indicate the relative position of the contact point between the resistive slide line element 53*a* and the wiper arm 50*a*', and also the angle between the respective distal end sections 6*aa*" and 6*ab*" of the restraining bar 6*a*'.

The electromechanical break/clutch mechanism 41*a* of the electromechanical hinge 21*a* can be controlled by pushing either a release or a brake button (not shown) on the control unit 10" which will respectively free the armature 47*a* to turn with respect to the stator coil 45*a* or attract the armature 47*a* to the stator coil 45*a* thereby preventing the armature 47*a* from turning with respect to the stator coil 45*a*. When the release button is pushed, the armature 47*a* is free to turn with respect to the coil 45*a* and the angle between the respective distal end sections 6*aa*" and 6*ab*" or 6*ba*" and 6*bb*" may be manually adjusted. In preferred embodiments, the change of the angle between the respective distal end sections can be monitored by watching an LCD readout display (not shown) on the control unit 10" as the angle is adjusted. When the angle reaches the desired angle, the brake may be applied by pushing the brake button, wherein a circuit is completed allowing an electric current to pass through the stator coil 45*a*, thereby creating a magnetic field which attracts the armature 47*a* and prevents the armature 47*a* from turning with respect to the coil 45*a*.

When the armature 47*a* is attracted to the coil 45*a*, as shown in FIG. 13, a pair of free riding annular disks 55*aa* and 55*ab* are gripped between the armature 47*a* and a stator housing 56*a* within the clutch housing 48*a*. The outer annular disk 55*ab* is preferably made of a suitable metal and the inner annular disk 55*aa* is preferably made of a suitable polymeric material to provide for a smooth gripping action between the respective surfaces and to prevent wear therebetween. The free riding disks 55*aa* and 55*ab* encircle a center portion of the armature 47*a*. A coil spring 31*a*' biases the armature 47*a* away from the stator housing 56*a* when the magnetic attraction between the coil 45*a* and the armature 47*a* is insufficient to overcome the mechanical force of the coil spring 31*a*' which biases the armature 47*a* away from the stator housing 56*a*.

In a preferred embodiment of the present invention, the electromechanical brake/clutch mechanism 41*a* is controlled by a microprocessor 64 (see FIG. 15) in the control unit 10" which is programmed to release the brake/clutch mechanism 41*a* after the completion of a specified number of isometric events or repetitions when the device 2" is set at a specific angle with respect to the respective distal end sections. Upon achieving a required number of isometric repetitions, the programmed microprocessor will release the brake and the angle between the respective end sections can be manually adjusted to a different angle. The program may further dictate how much the angle may be changed prior to breaking the electromechanical hinge 21*a* again and requiring further isometric repetitions at the new setting. In this manner an entire exercise routine can be controlled by the programmed microprocessor. Preferably, the mechanical movement of the electromechanical hinge 21*a* will be generated by force placed upon the device 2" by the individual engaged therein. However, the programmed microprocessor can be designed to place controls upon what movement will be allowed and when that movement will be allowed (i.e. after certain isometric event requirements have been met). It will be appreciated that such a system may be used to create a variety of exercise requirements which can individual will be encouraged to follow by his physician in order to conduct a proper exercise or rehabilitative routine.

Figure 15:
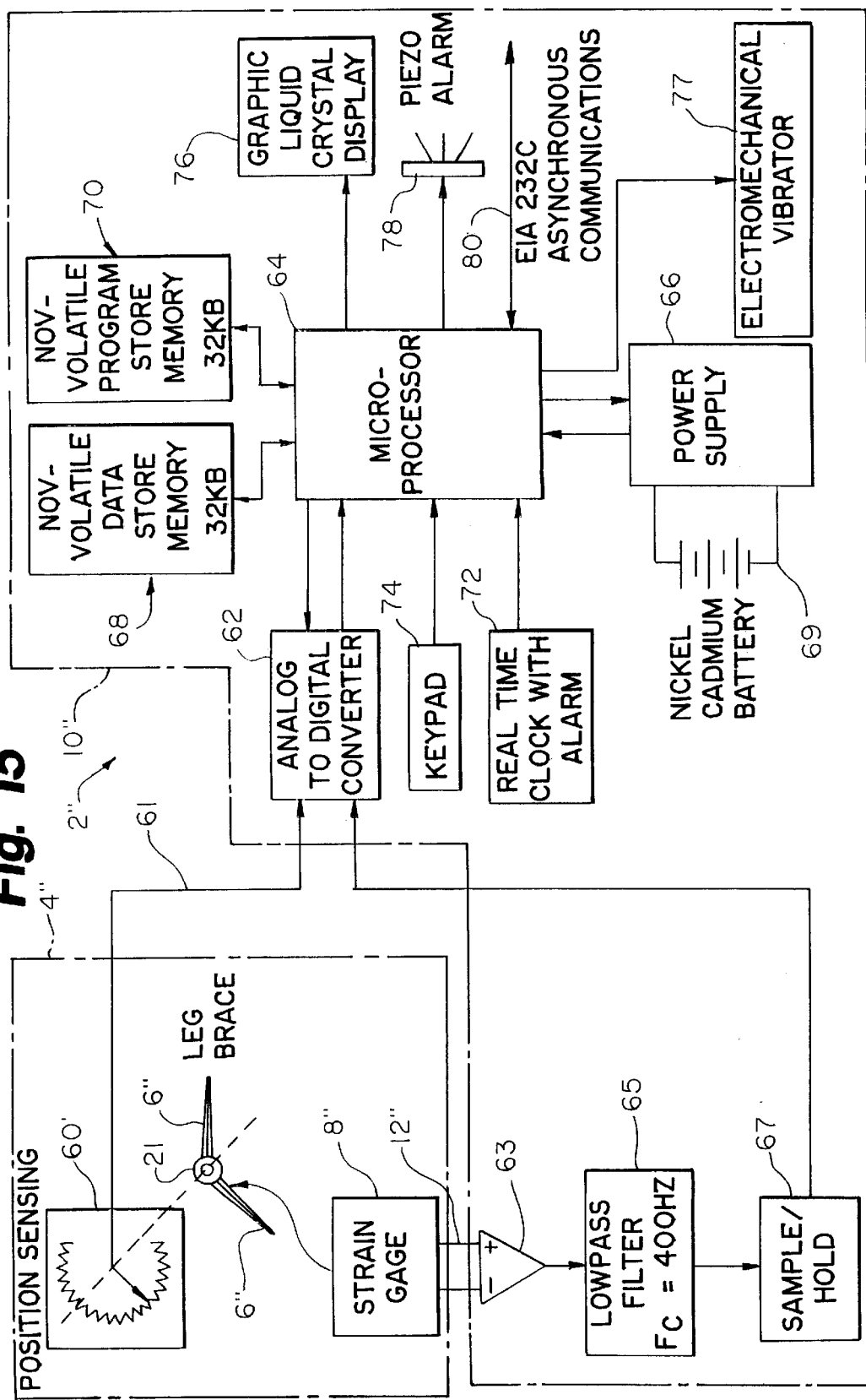
FIG. 15 is a functional block diagram of the orthopedic restraining device shown in FIGS. 11–14.

Illustrated in FIG. 15 is a functional block diagram of the control unit 10" of the orthopedic restraining device 2" shown in FIGS. 11–14. The control unit 10" preferably controls certain aspects of the operation of the orthopedic restraining device 2". The housing 4" of the orthopedic restraining device is represented by the broken line 4" and the control unit 10" is represented by the broken line 10". The various components of the control unit 10" are illustrated as being suitably electrically connected. The control unit 10" receives analog input signals from the position sensor 60' configured and arranged for sensing the relative angular position of the first and second distal end sections of the orthopedic restraining device 2", and the control unit 10' also receives signals from a stress sensing mechanism, in the embodiment shown the strain gauges 8", for sensing stress on the orthopedic restraining device 2". The signals received from the position sensor 60' are representative of the sensed relative angular position and the signals received from the strain gauges 8" are representative of the sensed stress. In the embodiment shown, control unit 10" shown thus receives two general types of input signals: one representative of the angular position of the orthopedic restraining device 2" and a second representative of the strain on the orthopedic restraining device. In some preferred embodiments, the position sensor 60' is suitably electrically connected to an analog to digital converter 62 which converts analog signals to digital signals. The strain gauges 8" are suitably electrically connected to the analog to digital converter 62. In the embodiment shown, the strain gauges 8" are illustrated as being interconnected to an amplifier 63 for amplification of the output signals from the strain gauges 8". In addition, the amplified signals output from the amplifier 63 are passed through a low pass filter 65 for filtering out background noise and other unwanted signal interference. In certain embodiments the signal frequency output from the low pass filter 66 is roughly four hundred (400) hertz (Hz). The output from the low pass filter function 65 is transferred to sample/hold circuitry 67 which periodically samples the output from the low pas filter 65 and then outputs the sensed electrical signal value to the analog to digital converter 62. The electrical connection between the strain gauges 8" in the housing 4" and the amplifier 63 in the control unit are represented by the reference numeral 12" while the electrical interconnection between the position sensor 60' and the analog to digital converter 62 is represented by the line 61. It will be appreciated that the amplifier, low pass filter, sample/hold, and analog to digital converter functions 63, 65, 67, 62 might be achieved by conventional well known circuitry.

The control unit 10" is further illustrated in FIG. 15 as including a microprocessor 64. It will be appreciated that numerous microprocessors might be utilized in keeping with the present invention; e.g. Intel 8088 and 8086. Motorola 6800, etc. The microprocessor 64 is shown as including a power supply 66 and a nickel cadmium battery 69. In addition to providing power to the control unit 10" in its operational state, and to a lesser degree, in its idle state, the power supply 66 also provides power to the electromechanical hinge 21, the position sensor 60' and the strain gauge or gauges 8". The microprocessor is also illustrated as including nonvolatile data memory 68 for storing data and nonvolatile program memory 70 for storing a control program. The memory 68 might be low power CMOS memory which can be read and written into and is powered by the battery 69. The memory 70 might be electrically programmable read only memory (EPROM). The control unit 10" is further illustrated as including a real time clock 72 including an alarm function. In alternate embodiments, a speaker and a voice synthesizer might be used to provide voice commands and information to the user. In addition, the control unit 10" is illustrated as including a keypad 74 for user input into the control unit. It will be appreciated that any number of user input devices might be utilized: e.g., a keypad having individual keys, a touch sensitive pad, etc. The control unit 10" is further illustrated as including a graphic liquid crystal display 76 for displaying graphics and text information and suitable user alerts. The display 76 can have various resolutions e.g., a 240 by 120 pixel display might be used. Once again, it will be appreciated that numerous display apparatus might be utilized in keeping with the present inventions. Additionally, the control unit 10" is illustrated as including a piezo alarm 78 for providing audible alerts to the user.

The control unit 10" is further illustrated as including an ETA 232 C asynchronous communications port 80 on the microprocessor 64 for enabling communications with the devices remote from the control unit 10". It will be appreciated that more than one communications port might be present and/or that multiple communication protocols might be utilized. There are several uses to which the communications port capability can be applied. For example, information can be down loaded from the microprocessor memory 68 to a printer/plotter for printout of selected information. In addition, data might be down loaded from the memory 68 of the microprocessor 64 to an external storage device having removable media so as to enable transfer of the data to a remote location. Yet in other embodiments, a communications port might provide for wireless transmissions from the microprocessor 64 to a remote host such as a microcomputer in the doctor's office or clinic. The communications port 80 might provide for interconnection to a modem such that the user patients can down load data into their doctor's computer system by use of to modem from their home or office. Still another application for a communications port would be to enable direct electrical connection between the microprocessor 64 and another computer. This would allow down loading of data from the memory 68 of the microprocessor 64 by interconnecting the microprocessor 64 to a suitable computer. For example, the user patient might come into the clinic on a periodic basis and have a technician connect the control unit 10" to a suitable computer in the clinic on a periodic basis and have a technician connect the control unit 10" to a suitable computer in the clinic and down load the data for analysis by the doctor while the user patient was at the clinic or at some later time. It will be appreciated that while the elements shown in FIG. 15, and discussed hereinabove, are described in terms of the embodiment shown in FIGS. 11–14, similar elements can be incorporated in the embodiment shown in FIGS. 3–10, and also in the embodiment shown in FIGS. 1 and 2 to the degree such elements are individually or collectively applicable thereto.

Figure 16A:
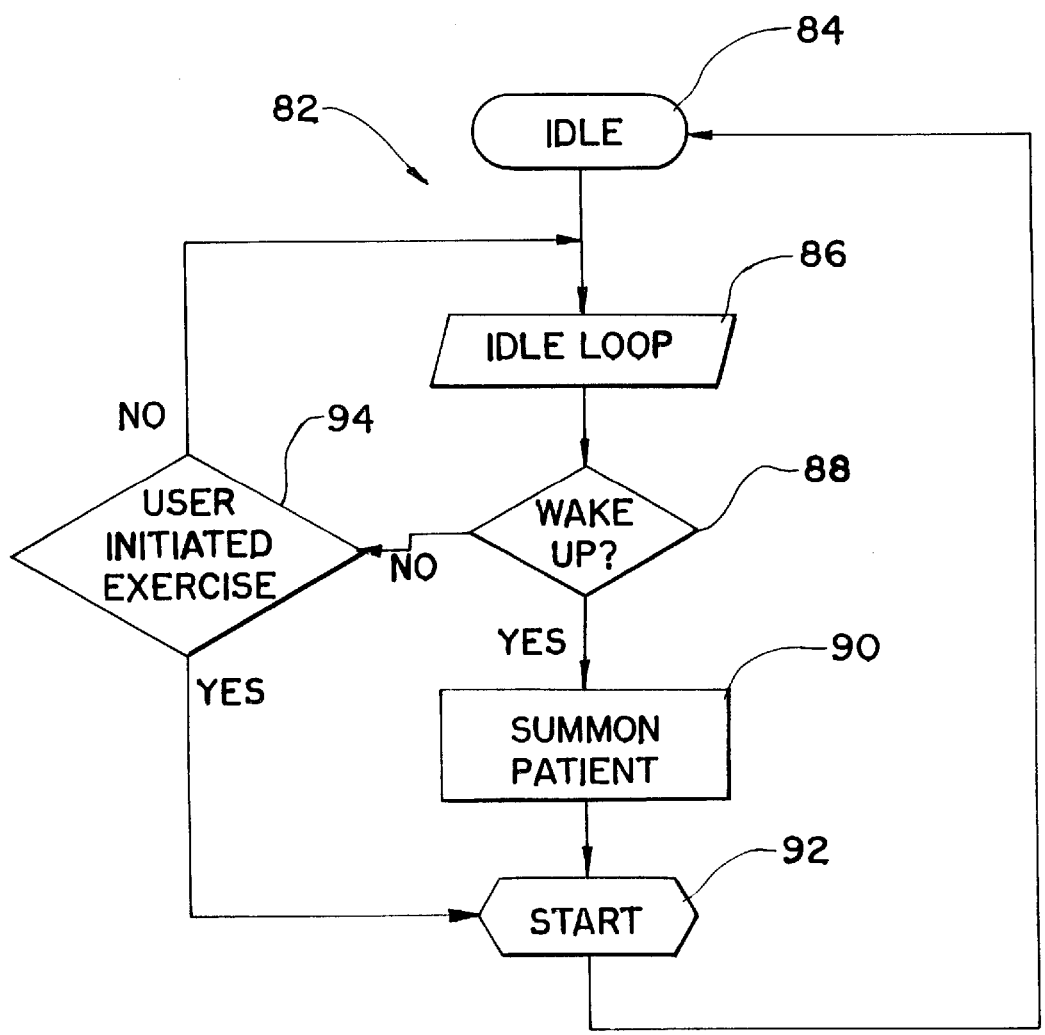

Referring now to FIGS. 16A through 16C there is illustrated a functional flow diagram of control logic for an orthopedic device in accordance with the principals of the present invention. It will be appreciated that numerous embodiments of the control logic might be implemented and yet be in keeping with the principals of the present invention. Moreover, various levels of capabilities and features can be incorporated into the control logic so as to provide the orthopedic restraining device 2" with a wide range of features and applications. In the embodiment shown, the control logic is embodied in control program 82 stored in the memory 70 of the microprocessor 64. In the embodiment shown, thirty-two kilobytes (32 kB) of memory storage is used for both data and the control program 82.

During typical operation, the control unit 10" will be in an idle state requiring minimal power. During this idle state, the control program 82 will periodically check the real time clock 72 to see if the elapsed time is such that it is time for the user patient to exercise. This is best illustrated in FIG. 16A wherein the control program will go into an idle loop for a predetermined period of time. A check is then made at block 88 to see if the elapsed time is such that it is time for the user patient to exercise. If this is the case, then at block 90 the control program 82 will summon the patient by use of an audible, palpable and/or a visual alarm. The audible alarm might be executed by use of the piezo alarm 78 as illustrated in FIG. 15. The visual alarm might take the form of a flashing indicator or the like on the display 89. A palpable alarm could take the form of a common electromechanical vibrator 77. After summoning the patient at block 90, the control program 82 at block 92 then calls on a start subroutine illustrated in FIG. 16B. At block 88, if it is not yet time to summon the patient, the control program 82 at block 94 checks to determine if the user patient has initiated an exercise. If at block 84 the user has requested initiation of an exercise then the control program 82 calls on the start subroutine at block 92. However, if the user has not initiated an exercise, then the control program 82 returns to the idle loop. It will be appreciated that in some embodiments of the present invention, both of the function represented by blocks 94 and 88 may not be present. For example, if the doctor does not want the patient to initiate his/her own exercise, the function represented by block 94 might be deleted from the control program 82. In this case, at block 88, if it is not yet time to summon the patient, the control program once again returns to the idle loop 86. In yet other embodiments, the user patient might be allowed to initiate exercise only if the torque (foot pounds of force) selected by the user patient to be applied by the user is within a predetermined limit. If this were the case, there would be an additional logic clock to see if the related torque was within the guidelined limit. It will be appreciated that various alternative scenarios might be utilized and still be in keeping with the principles of the present invention.

The control logic for an embodiment of the start subroutine 92 is illustrated in FIG. 16B. The start subroutine begins at block 96. At block 98 the control unit 10" powers up to a full operational power level and initializes the hardware including the sensors of the orthopedic restraining device 2". At block 99, the control program 82 enters a subroutine named MAIN which is a menu display subroutine for displaying various menus on the display 76. At block 100 a main menu selection displaying various user patient options/modes of operation is displayed on the display 76. In the embodiment shown, the following options are displayed as the main menu: Help, Setup, Exercise and Statistics. The control program 82 then checks if the user patient has made a selection within a predetermined period of time; e.g., one minute, at block 102. If no user patient selection occurs within this predetermined time interval, the control program 82 then turns off the control unit 10", i.e., powers the control unit 10" down to its idle state, at block 104. At block 106 the control program 82 returns to the idle state and will remain there until it is time to summon the user patient for a scheduled exercise or until the user patient initiates an exercise. At block 108 a check is made if the user patient has selected the help option. If the user has selected the help option, then at block 110 the control program 82 displays the various help screens one at a time. The help screens will provide the user patient with the information necessary to operate the control unit 10". If the help option was not selected by the user at block 108, then at block 112 the control program 82 checks to see if the user patient selected the setup option. If the user patient has selected the setup option at block 112, then at block 114 the display prompts the user patient to select the number of exercise repetitions, which the user patient does at that time.

At block 116 the display prompts the user to select the force (torque to be applied, which the user does at that time. In alternate embodiments, the force (torque) to be applied is present by the prescribing professional. The number of repetitions and torque preferably have a default value which is preset by the doctor or prescribing professional. In some embodiments, after being preset, the user will not be able to change these default values. It will be appreciated that various parameters and restrictions might be placed on the setup functions of the control program 82. For example, the patient might be allowed to select from within predetermined parameters the number of repetitions and the force (torque) to be applied. The control program 82 might be programmed to vary the number of repetitions and force (torque) requirement throughout the user patient's recovery/exercise term. The setup options might be limited such that the patient can only select additional exercise and not less than that prescribed by the doctor. Moreover, the patient might be forced to select within a range of force (torque) values. In the preferred embodiment, the orthopedic restraining device 2 has an operational torque range of from zero to one thousand foot pounds. It will be appreciated that, in alternate embodiments, this range might vary depending upon the joint being exercised and/or the parameters specified by the healthcare professional. The keypad 74 will preferably include numeric keys, direction keys, and other predetermined function keys such as an enter key to enter the selected value. The selected number of repetitions, number of exercise times per day, time of day to exercise, etc. might be selected by using up, down, and sideways keys with the enter key being used to enter a selected value into the system.

Next the control program 82 checks to see if the exercise option is selected by the user patient at block 118. If the exercise menu is selected at block 118, then at block 120 the control program 82 calls on an exercise subroutine, an embodiment of which is illustrated in FIG. 16C. If the exercise option is not chosen at block 118, then at block 122 the control program 82 checks if the statistics option is selected by the user patient. If the statistics option is chosen by the user patient, then at block 124 various statistical information is displayed on the display 76 with sensed stress data obtained from a prior exercise. If the statistics option was not chosen at block 122, then at block 123, the control program 82 checks to see if the user patient has selected the off option so as to exit the menu display subroutine. If so, at block 125, the control program 82 powers the control unit 10" down to its idle state. At block 127, the control program 82 returns to the idle state. The control program 82 will then return to displaying the main menu at block 99. It will be appreciated that numerous types of statistical displays might be provided to the user on the display 76. For example, a curve might be displayed wherein the area under the curve represents the work done (total energy exerted) by the patient during a particular exercise cycle. Yet another type of statistical display might be a display of the variance between the exercise goal and the actual exercise accomplished. Moreover, much more elaborate statistical analysis might be provided at a host computer such that upon down loading the data from the control unit 10", the host computer can provide a number of different statistical analyses.

An embodiment of the exercise subroutine is illustrated in FIG. 16C the exercise subroutine begins at block 126. At block 128, the control program 82 initializes the exercise display presentation which is displayed on the liquid crystal display 76. At block 130, the control program 82 checks if the user patient has begun an exercise repetition. This is determined by sensing a force (torque) being exerted by the user patient in the proper direction. Once the user patient has started a repetition at block 132 the control program 82 will take a predetermined quantity of signal readings as received from the analog digital converter 62 and average them. At block 134, the control program 82 will display the readings from the strain gauges as the strain sensed by the strain gauges 8. In one embodiment, the signal readings are averaged. The averaged signals are then displayed as a bar graph or a histogram on the display 76. At block 136, the control program 82 sounds a tone at a frequency corresponding to a percent of the targeted exercise force (torque) be exerted by the user patient and will sound a continuous tone if the user patient achieves the targeted exercise force. At block 138 the control program 82 will check to see if the user patient has finished a particular repetition. If not the control program 82 will continue to take readings and averaging them. If the repetition is finished, then at block 140, the control program 82 will check if the user patient has completed the number of repetitions designated by the doctor and/or selected by the user patient. If the user patient has not finished his/her repetitions, then at block 142 the repetition counter is incremented and the control program 82 continues taking readings. Between repetitions, the control program 82 calculates the work or energy exerted by the user patient and might display the energy exerted as a percentage of the targeted energy amount. Stress data obtained during the exercise is saved or recorded for subsequent statistical analysis, displaying, recording and/or downloading to another computer. If the user patient has finished the designated number of repetitions, then at block 144 the exercise program 82 returns to the start program in FIG. 16B at the location where it initiated the exercise program such that the start program continues its normal execution and will check at block 122 to see if the statistics option was chosen.

From the above discussion it will be appreciated, that the control unit 10" might have various levels of functions. In the most basic configuration the control unit 10" might simply indicate sensed stress, display data and/or store data. Additionally, although in the preferred embodiment of the control unit 10" mounted on the housing 4" includes all the features shown in FIG. 15, it will be appreciated that some of these features might not be present and/or that other features might be contained in a separate ambulatory housing which is interconnected to the control unit 10" when desired. For example, the keyboard and display features might be present in a separate hand held housing. Alternatively, the entire control unit 10" can be wired or wirelessly interconnected for receiving outputs from the strain gauge or gauges 8", and/or other elements of respective embodiments of the present restraining device, only when desired by the user.

Figure 18:
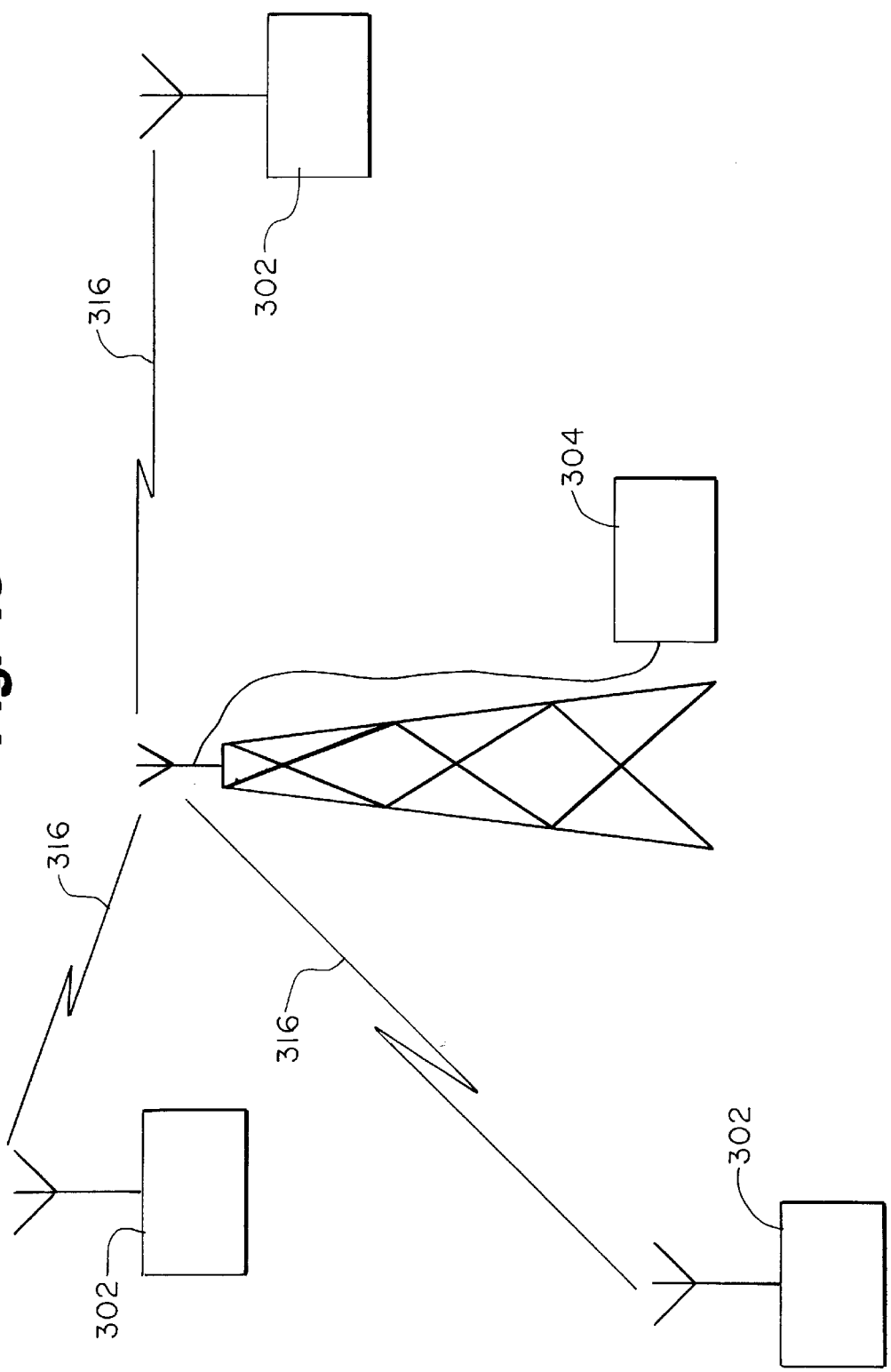
FIG. 18 is a block diagram showing the preferred embodiment communication system shown in FIG. 17 at a high level view.

Referring now to FIG. 17, a block diagram of a preferred embodiment communication system 300 in accordance with the present invention for use with an instrumented orthopedic restraining device 2 (e.g., a brace) is shown. The following discussion will focus on the operations of a single remote communication unit 302 and a central site monitoring station 304 in communicating an orthopedic parameters signal over a radio communication channel. However, it will be appreciated by those skilled in the art that several remote communication units 302, as shown in FIG. 18 may be used in conjunction with a single radio coverage area of the central station 304. In addition, several central stations 304 can be connected together to form a network such that a larger radio coverage area can be used by the remote communication units 302.

The remote communication unit 302 includes a data input 306 which receives an orthopedic parameters signal representative of a sensed stress work valve, or other parameter indicative of specific effort in a personal orthopedic restraining device 2 from the restraining device output port 80'. The sensed stress preferably is a value representative of a total torque output by the individual over a period of time as measured by the personal orthopedic restraining device 2. The restraining device 2, previously described in reference to FIGS. 1–16 is designed to restrain movement of a first flexibly connected body portion relative to a second flexibly connected body portion of an individual who is wearing the restraining device. It should be noted that asynchronous serial port 80 can take many other forms including a parallel port, Personal Computer Memory Card International Association (PCMCIA) interface, or RJ-11 phone jack; however, for the purposes of the following discussion an RS-232 serial port 80 is assumed to be used as the data output 80' and data input 81' line of the restraining device 2.

The data input 306 preferably includes a mechanism (e.g., buttons, a keypad, touch screen, or the like (not shown)) for incorporating messages obtained from the individual into the orthopedic parameters signal for transmission to the central site monitoring station 304. In addition, the orthopedic parameters signal preferably further includes a patient identifier which can be used to identify a particular set of data from a patient at the central station 304 from among several other sets of data pertaining to other patients. By way of example, it will be assumed that the orthopedic parameters signal contains 1200 data bits of information. It will be appreciated by those skilled in the art that this choice of 1200 data bits is only to facilitate the following discussion. The orthopedic parameter signal can readily contain more or less data bits while not departing from the scope and spirit of the present invention.

An encoder 308 is operatively coupled to the data input 306 to protect the received orthopedic parameters signal from potential transmission errors by encoding the received orthopedic parameters signal. It will be appreciated by those skilled in the art that several encoding techniques exist including interleaving, block coding, convolutional coding, and cyclical redundant coding. The optimal encoding techniques for a particular communication system vary depending upon many factors including the particular medium upon which the communication is to travel, the environment, the transmit power level, the available bandwidth, and the level of tolerance for errors. For the preferred embodiment of the present invention a convolutional coding scheme along with interleaving is used to provide maximum protection against data loss due to transmission errors.

In continuing the example, the 1200 data bits of the orthopedic parameters signal can be convolutionally encoded at a fixed encoding rate of one data bit to three data symbols such that 3600 data symbols are generated. It will be appreciated that convolutional encoding facilitates the use of powerful detection techniques such as maximum likelihood decoding which not only detect, but also correct errors in the transmitted data bits. To further enhance the protection of the data bits, the 3600 data symbols are block interleaved through a 36 by 100 symbol matrix (i.e., 36 columns and 100 rows). The data symbols are individually input in the matrix into locations within the matrix so that the matrix is filled in a column by column manner. The data symbols are individually output from locations within the matrix so that the matrix is emptied on a row by row manner. This particular matrix shape is chosen to increase the output interleaving distance between the consecutively input non-interleaved data symbols. During this encoding process, a cyclical redundant code (CRC) and padding may be added to ease the operation of encoder 308 and help aide in the detection of transmission errors.

A modulator 310 is operatively coupled to the encoder 308 to prepare the encoded orthopedic parameters signal for subsequent transmission by modulating the encoded orthopedic parameters signal. Several forms of modulation exist. The encoded orthopedic parameters signal can be modulated according to a communication access type selected from the group consisting of: frequency division multiple access, time division multiple access, and code division multiple access. For the preferred embodiment, direct sequence code division multiple access (DS-CDMA) modulation is used and as such the encoded orthopedic parameters signal is directly spread with a spreading code.

In continuing the example, the 3600 data symbols (i.e., encoded orthopedic parameters signal) are spread with a 65,536 symbol long spreading code which is generated each second (i.e., generated at a 65.536 kilosymbols/second rate). The spreading process is accomplished by using a modulo-two adder/mixer to merge the data symbols with the spreading code which results in a modulation sequence. If the original 1200 data bits were received at the data input 306 at a 9600 bits/second rate and convolutionally encoded by a ⅓ encoder 308, then the spreading process results in 8192 bit long sequence that span over a 125 millisecond time period.

Further, a transmitter 312 is operatively coupled to the modulator 310 to transmit the modulated orthopedic parameters signal over a communication channel 316 by radiating a radio signal on antenna 314 such that movement of flexibly connected body portions can be monitored by the central site monitoring station 304. The communication channel 316 may be one of several types of channels including: an electronic data bus, radio communication link, wireline, optical fiber link, and/or satellite link. The type of communication channel 316 can also be described which reference to a particular channel known in the art. Some of the possible currently existing channels that may be used include a serial port wireline, a parallel port wireline, a public switched telephone network (PSTN), a private data network, a radio data network, a paging channel, a short message service channel, a personal communications service channel, a trunked radio channel, a cellular radio channel, and/or a satellite link. For the preferred embodiment, a radio communication link on a radio data network is used as the communication channel 316.

Referring back to the example, the 8192 bit long sequence is used to bi-phase modulate a sinusoid by driving the phase controls of the sinusoid. The sinusoid output signal is bandpass filtered, translated to a radio frequency (RF), amplified, filtered, and radiated by the antenna 314 to complete transmission of the orthopedic parameters signal in the communication channel 316 with binary phase shift keying (BPSK) modulation.

The communication unit 302 also includes a detachable connection mechanism 326 for selectively connecting the communication unit 302 to the personal orthopedic restraining device 2. This will allow the patient to attach the communication unit 302 only when needed as well as provide for easy replacement of the communication unit 302 should it need repair or maintenance. The communication unit 302 also has a power supply 66 (e.g., a rechargeable battery) which is detachably connected to the personal orthopedic restraining device 2 and the communication unit 302 by connector 328. The power supply 66 preferably is shaped and arranged for optimal positioning on the individual which will be wearing the personal orthopedic restraining device 2 and the communication unit 302.

In some instances, it may be necessary for the individual wearing the restraining device 2 to get a message from the central station 304 or for the communication unit/restraining device 2, 302 to receive instructions from the central station 304. Therefore, the communication unit 302 is also configured with a receiver 318 for receiving a communication from the central site monitoring station 304 over the communication channel 316. The central site monitoring station communication may take many forms including: a message to the individual wearing the personal orthopedic restraining device 2 and the communication unit 302, a programming instruction for the personal orthopedic restraining device 2, a request for an orthopedic parameter signal from the personal orthopedic restraining device 2, a request to resend a portion of an orthopedic parameter signal previously sent by the personal orthopedic restraining device 2, and/or confirmation that a previous orthopedic parameter signal was received. As a result of some of these communications, the communication unit 302 may need to provide the central site monitoring station communication to the personal orthopedic restraining device 2 and as a data output 324 is provided for such purposes.

The receiving operations are performed in the reverse order from that which was done for the transmitting operations. In particular receiver 318 performs initial channel acquisition and samples a received modulated orthopedic parameters signal into data samples. By way of example, it is assumed that a communication signal similar to the one described above in reference to the transmitting operations is received. This communication signal is BPSK sampled such that a 8192 bit long sequence of data samples is received.

Demodulator 320 is operatively coupled to the receiver 318 to demodulate the received modulated orthopedic parameters signal. In the example, the 8192 data samples are correlated to the known 65,536 symbol long spreading code used in the transmitting operations such that 3600 demodulated data samples are generated.

A detector 322 is operatively coupled to the demodulator 320 to detect an orthopedic parameters signal from demodulated orthopedic parameters signal. In the example, the detector 322 deinterleaves the 3600 demodulated data samples by loading them in a 36 column by 100 row matrix in a row by row manner and subsequently emptying the matrix in a column by column manner. The 3600 deinterleaved demodulated data samples are then used by the detector 322 as soft decision data in a maximum likelihood decoding operation. The decoding operation can also detect transmission errors in the demodulated orthopedic parameters signal such that a request can be made to the transmitting party to resend the communication is an error is detected. In addition, if a maximum likelihood sequence estimation (MLSE) algorithm such as a Viterbi decoding algorithm is used then some correction of transmission errors in the demodulated orthopedic parameters signal is possible. For MLSE detection, the 3600 bits of soft decision data form a set of soft decision transition metrics. These transition metrics are used at each particular time state of the MLSE decoder. The number of soft decision metrics in each set is equal to two raised to the power of the number of input data bits originally used in the convolutional encoding process which is in this case three bits. Therefore, two raised to the power of three or eight bits of transition metrics are used at each time state in the MLSE based detector 322 to generate 1200 estimated/detected orthopedic parameters signal data bits.

A data output 324 is operatively coupled to the detector 322 to provide the detected orthopedic parameters signal to the personal orthopedic restraining device 2 via the input line 80" of port 80.

A central site monitoring station communication unit 304 also is provided in the preferred embodiment communication system 300. The central site monitoring station communication unit 304 in a manner substantially similar to the that which was described above for the remote communication unit 302. The central site monitoring station communication unit 304 includes a receiver 332 for receiving a modulated orthopedic parameters signal from a personal orthopedic restraining device 2 worn by an individual via antenna 330. The modulated orthopedic parameters signal is representative of a sensed stress in the restraining device 2. A demodulator 334 is operatively coupled to the receiver 332 to demodulate the received modulated orthopedic parameters signal. A detector 336 is operatively coupled to the demodulator 334 to detect an orthopedic parameters signal from demodulated orthopedic parameters signal. The receiver 332, demodulator 334, and detector 336 operate substantially the same as that which was described for the receiver 318, demodulator 320, and detector 322 of the remote communication unit 302. In place of a data output, the central station 304 includes a processor 338 operatively coupled to the detector 336 which performs the operations of a data output by providing the detected orthopedic parameters signal to an external device (not shown) via communication link 340 such that subsequent processing of the orthopedic parameters signal can be performed.

As previously noted with respect to the remote communication unit 302 attached to the restraining device 2, the central site monitoring station communication unit 304 preferably is adapted for use with a variety of different types of communication channels and different modulation schemes. Also, the detector 336 preferably includes a mechanism for detecting transmission errors in the demodulated orthopedic parameters signal. In addition to detecting the errors, the detector 336 preferably includes a mechanism for correcting some types of transmission errors in the demodulated orthopedic parameters signal based on a maximum likelihood sequence estimation algorithm.

The central site monitoring station communication unit 304 also includes a transmitter 346 for transmitting a communication from the central site monitoring station 304 over the communication channel 316 to the personal orthopedic restraining device 2. This communication, as previously noted, can have several different contents, including: a message to the individual wearing the personal orthopedic restraining device 2 and the communication unit 302, a programming instruction for the personal orthopedic restraining device 2, a request for an orthopedic parameter signal from the personal orthopedic restraining device 2, a request to resend a portion of an orthopedic parameter signal previously sent by the personal orthopedic restraining device 2, and/or confirmation that a previous orthopedic parameter signal was received. Encoder 342 receives a communication which is to be sent to the remote communication unit 302 or the personal orthopedic device 2 from the processor 338 which is coupled to the encoder 342. A modulator 344 is operatively coupled to the encoder 342 and to the transmitter 346. The operations of the encoder 342, modulator 344, and transmitter 346 are substantially the same as that which was described for the encoder 308, modulator 310, and transmitter 312 of the remote communication unit 302.

As previously noted, it may be desirable for subsequent processing to be done to communications received from the personal orthopedic restraining device 2 and as such an external device (not shown) can be coupled to the central site monitoring station communication unit 304 via communication link 340. Some limited processing can also be performed by processor 338 within the central station communication unit 304. Either, the processor 338 or the external device preferably processes the orthopedic parameters signal. This orthopedic parameters signal is a sensed stress value representative of a total torque output by the individual over a period of time as measured by the personal orthopedic restraining device 2. Some of the types of subsequent processing that either the processor 338 or external device may perform include: comparing the sensed stress value to an expected value to confirm that the individual's responses are within norms, comparing the sensed stress value to previously received values associated with a patient identifier for the individual to judge the individual's response to treatment, storing the sensed stress value along with previously received values associated with a patient identifier for the individual to create a clinical record, monitoring a prescribed exercise regimen of the individual based on the sensed stress value to monitor compliance with the prescribed exercise regimen, performing statistical analysis of the sensed stress value in conjunction with other values received at the central site monitoring station, providing a message obtained from the individual wearing the personal orthopedic device 2 to another individual at the central site monitoring station 304, and/or determining a programming instruction to be sent to the personal orthopedic restraining device 2. The clinical record may be useful for insurance, patient billing, or a potential practice standard review of the patient's case. In addition, the programming instructions may include modifications to the exercise regimen or adjustments to the reporting schedule.

Figure 19:
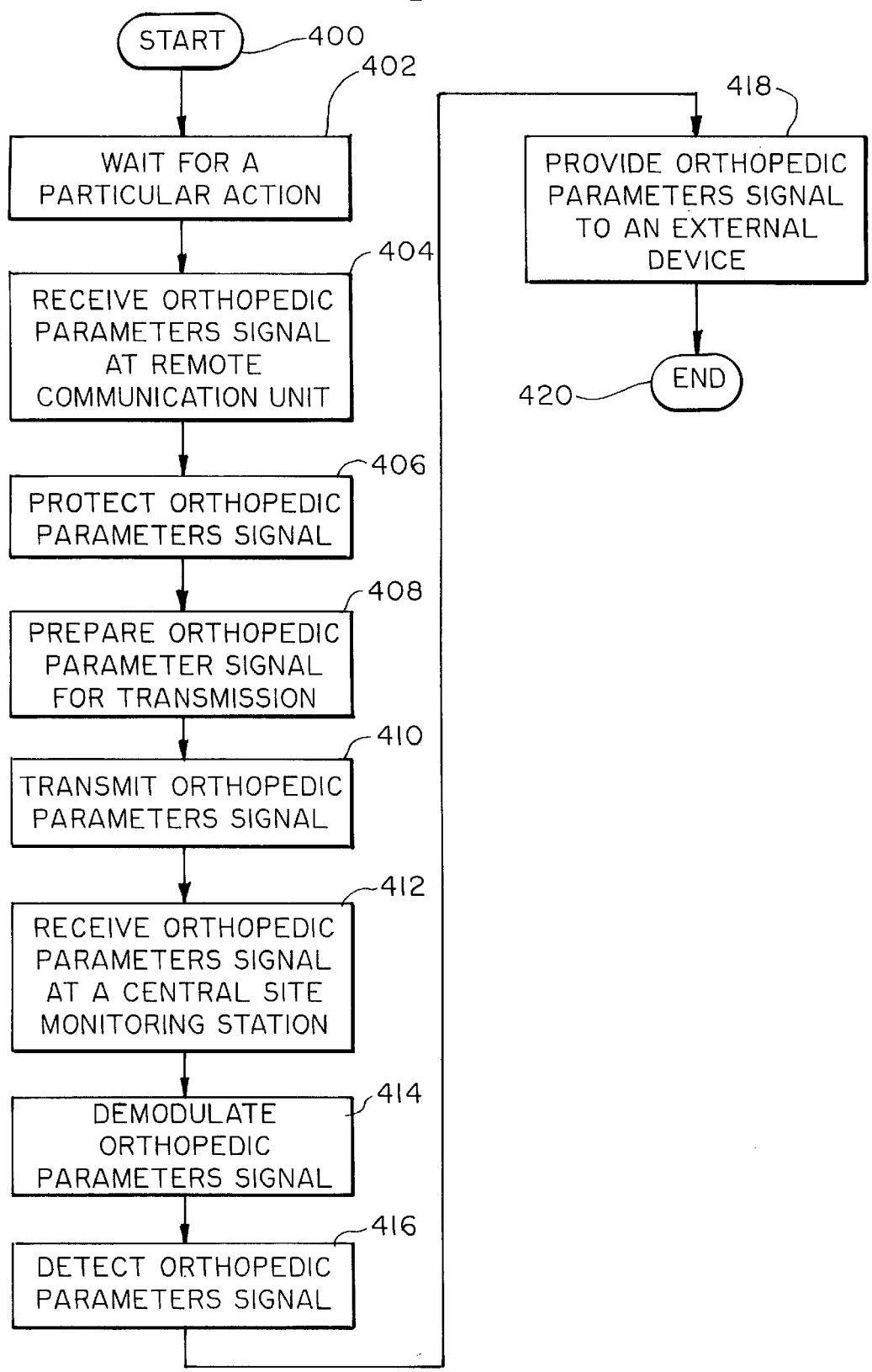
FIG. 19 is a flowchart of the preferred embodiment one-way operations of the communication system as shown in FIG. 17 in accordance with the present invention.

The present invention also can be described in reference to a device-implemented method steps 400–420 shown in FIG. 19 which detail preferred embodiment one-way operations of the communication system 300 as shown in FIG. 17. This one-way method of communicating an orthopedic parameters signal between a remote communication unit 302 and a central site monitoring station 304 can be used when only transmissions from the restraining device 2 and to the central station 304 are possible. The orthopedic parameters signal includes at least one value representative of a total torque output by an individual over a period of time as measured by a personal orthopedic restraining device 2. The restraining device 2 being of the type which restrains movement of a first flexibly connected body portion relative to a second flexibly connected body portion of an individual.

This communication method includes waiting 402 for a particular action to occur. This particular action may be any one of a number of different actions, including: the completion of a prescribed exercise regimen, the instance of a required periodic reporting time, the generation of two or more different orthopedic parameters signals by the personal orthopedic device, and/or a message being obtained from the individual for incorporation into the orthopedic parameters signal for transmission to the central site monitoring station 304.

Subsequent to the particular action occurring, the orthopedic parameters signal is received 404 at the remote communication unit 302 from the personal orthopedic restraining device 2. The received orthopedic parameters signal is protected 406 from potential transmission errors by encoding the received orthopedic parameters signal. The encoded orthopedic parameters signal is prepared 408 for subsequent transmission by modulating the encoded orthopedic parameters signal. Then, the modulated orthopedic parameters signal is transmitted 410 over a communication channel 316 from the remote communication unit 302 and to the central site monitoring station 304 such that movement of flexibly connected body portions can be monitored by the central site monitoring station 304.

The modulated orthopedic parameters signal is received 412 at the central site monitoring station 304 from over the communication channel 316. The received modulated orthopedic parameters signal is demodulated 414. An orthopedic parameters signal is detected 416 from demodulated orthopedic parameters signal. Finally, the detected orthopedic parameters signal is provided 418 to an external device such that subsequent processing of the orthopedic parameters signal can be performed.

Figure 20:
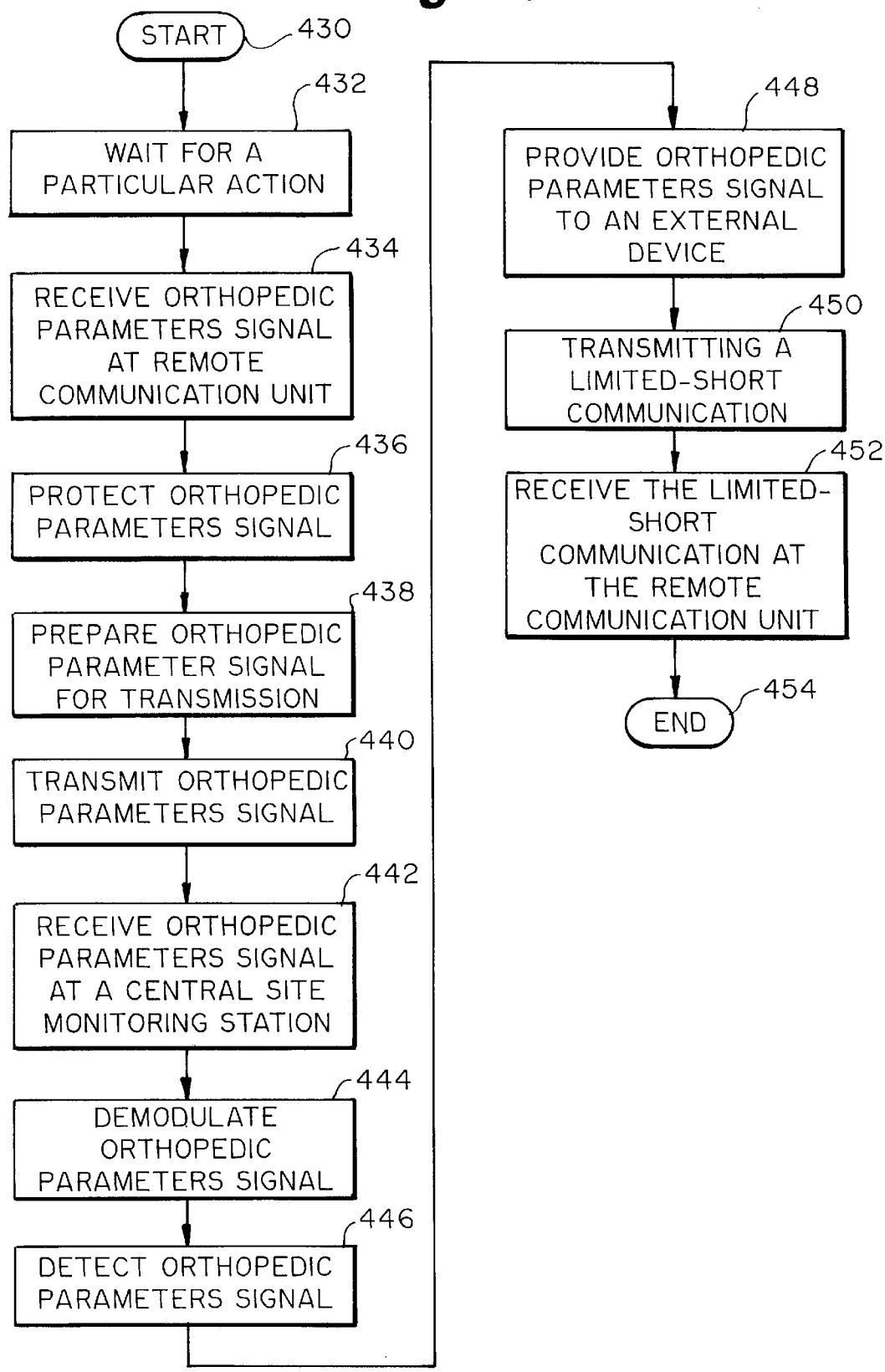
FIG. 20 is a flowchart of the preferred embodiment limited two-way operations of the communication system as shown in FIG. 17 in accordance with the present invention.

The present invention also can be described in reference to a device-implemented method steps 430–454 shown in FIG. 20 which details an alternative preferred embodiment limited two-way operations of the communication system 300 as shown in FIG. 17. This limited two-way method of communicating an orthopedic parameters signal between a remote communication unit 302 and a central site monitoring station 304 can be used when full bandwidth transmissions from the restraining device 2 and to the central station 304 are possible and some limited communication is possible in the reverse direction. The orthopedic parameters signal includes at least one value representative of a total torque output by an individual over a period of time as measured by a personal orthopedic restraining device 2. The restraining device 2 being of the type which restrains movement of a first flexibly connected body portion relative to a second flexibly connected body portion of an individual.

This communication method includes waiting 432 for a particular action to occur. This particular action may be any one of a number of different actions, including: the completion of a prescribed exercise regimen, the instance of a required periodic reporting time, the generation of two or more different orthopedic parameters signals by the personal orthopedic device, a message being obtained from the individual for incorporation into the orthopedic parameters signal for transmission to the central site monitoring station 304 and/or a communication being received from the central site monitoring station 304 which requests an orthopedic parameter signal from the personal orthopedic restraining device 2.

Subsequent to the particular action occurring, the orthopedic parameters signal is received 434 at the remote communication unit 302 from the personal orthopedic restraining device 2. The received orthopedic parameters signal is protected 436 from potential transmission errors by encoding the received orthopedic parameters signal. The encoded orthopedic parameters signal is prepared 438 for subsequent transmission by modulating the encoded orthopedic parameters signal. Then, the modulated orthopedic parameters signal is transmitted 440 over a communication channel 316 from the remote communication unit 302 and to the central site monitoring station 304 such that movement of flexibly connected body portions can be monitored by the central site monitoring station 304.

The modulated orthopedic parameters signal is received 442 at the central site monitoring station 304 from over the communication channel 316. The received modulated orthopedic parameters signal is demodulated 444. An orthopedic parameters signal is detected 446 from demodulated orthopedic parameters signal. The detected orthopedic parameters signal is provided 448 to an external device such that subsequent processing of the orthopedic parameters signal can be performed. A limited-short communication is transmitted 450 from the central site monitoring station 304 over the communication channel 316 to the personal orthopedic restraining device 2. The limited-short communication may take many forms, but preferably includes: a request for an orthopedic parameter signal from the personal orthopedic restraining device 2, a request to resend a portion of an orthopedic parameter signal previously sent by the personal orthopedic restraining device 2, and/or confirmation that a previous orthopedic parameter signal was received. Finally, the limited-short communication is received 452 at the remote communication unit 302 from over the communication channel 416.

Figure 21:
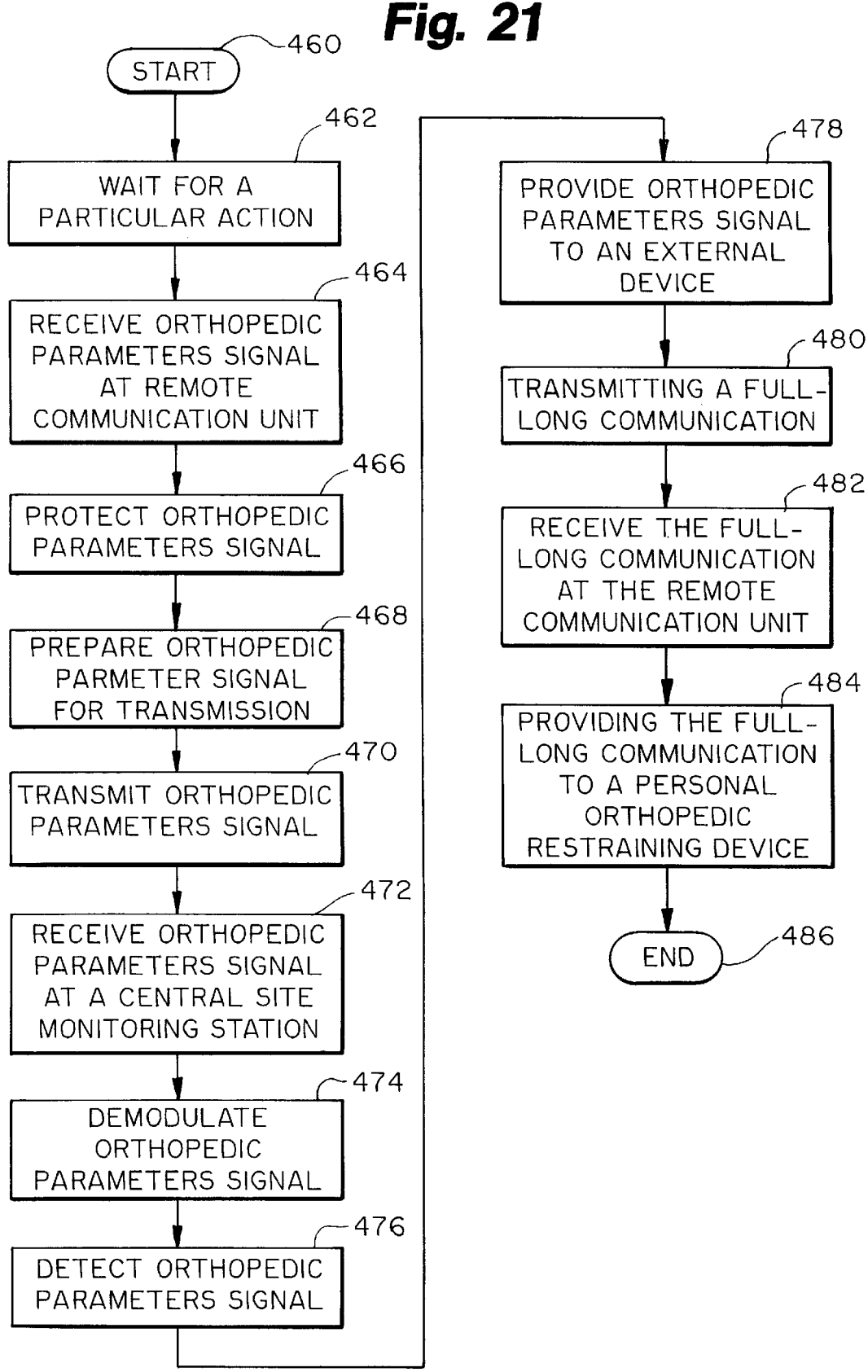
FIG. 21 is a flowchart of the preferred embodiment full two-way operations of the communication system as shown in FIG. 17 in accordance with the present invention.

The present invention also can be described in reference to a device-implemented method steps 460–486 shown in FIG. 21 which details an alternative preferred embodiment full two-way operations of the communication system 300 as shown in FIG. 17. This full two-way method of communicating an orthopedic parameters signal between a remote communication unit 302 and a central site monitoring station 304 is by far the most useful, but also the most complex. It can be used when full bandwidth transmissions in both directions between the restraining device 2 and to the central station 304 are possible. The orthopedic parameters signal includes at least one value representative of a total torque output by an individual over a period of time as measured by a personal orthopedic restraining device 2. The restraining device 2 being of the type which restrains movement of a first flexibly connected body portion relative to a second flexibly connected body portion of an individual.

This communication method includes waiting 462 for a particular action to occur. This particular action may be any one of a number of different actions, including: the completion of a prescribed exercise regimen, the instance of a required periodic reporting time, the generation of two or more different orthopedic parameters signals by the personal orthopedic device, a message being obtained from the individual for incorporation into the orthopedic parameters signal for transmission to the central site monitoring station 304 and/or a communication being received from the central site monitoring station 304 which requests an orthopedic parameter signal from the personal orthopedic restraining device 2.

Subsequent to the particular action occurring, the orthopedic parameters signal is received 464 at the remote communication unit 302 from the personal orthopedic restraining device 2. The received orthopedic parameters signal is protected 466 from potential transmission errors by encoding the received orthopedic parameters signal. The encoded orthopedic parameters signal is prepared 468 for subsequent transmission by modulating the encoded orthopedic parameters signal. Then, the modulated orthopedic parameters signal is transmitted 470 over a communication channel 316 from the remote communication unit 302 and to the central site monitoring station 304 such that movement of flexibly connected body portions can be monitored by the central site monitoring station 304.

The modulated orthopedic parameters signal is received 472 at the central site monitoring station 304 from over the communication channel 316. The received modulated orthopedic parameters signal is demodulated 474. An orthopedic parameters signal is detected 476 from demodulated orthopedic parameters signal. The detected orthopedic parameters signal is provided 478 to an external device such that subsequent processing of the orthopedic parameters signal can be performed. A full-long communication is transmitted 480 from the central site monitoring station 304 over the communication channel 316 to the personal orthopedic restraining device 2. The full-long communication may take many forms, but preferably includes: a message to the individual wearing the personal orthopedic restraining device 2 and the communication unit 302, a programming instruction for the personal orthopedic restraining device 2, a request for an orthopedic parameter signal from the personal orthopedic restraining device 2, a request to resend a portion of an orthopedic parameter signal previously sent by the personal orthopedic restraining device 2, and/or confirmation that a previous orthopedic parameter signal was received. Subsequently, the full-long communication is received 482 at the remote communication unit 302 from over the communication channel 416. Finally, if appropriate, the full-long communication is provided 484 to the personal orthopedic restraining device 2.

For either the one-way, limited two-way, or full two-way communication schemes, the device-implemented methods also preferably include connecting the remote communication unit 302 to the personal orthopedic restraining device 2 prior to performing the receiving step 404, 434, or 464. Similarly, either of the two-way device-implemented methods also preferably include connecting the remote communication unit 302 to a communication channel coupler prior to performing the transmitting step 450 or 480. The communication channel coupler being configured for use with a particular type of communication channel, including: an electronic data bus, radio communication link, wireline, optical fiber link, and/or satellite link.

Also, any of the device-implemented methods preferably includes storing two or more different orthopedic parameters signals before transmitting any signals such that modulated versions of the stored two or more orthopedic parameters signals are transmitted in a single transmission burst over the communication channel 316. This storing technique can be used to reduce the overall power consumption of a communication unit 302 by reducing the average number of transmissions that a communication unit 302 performs in a given time period.

A primary problem in orthopedic surgery is the complexity with which weakness, muscle weakness in particular, compounds pain or other injury. A person who has, for example, a patellofemoral problem may be able to tolerate the pain which the patellofemoral problem causes, but they cannot tolerate the long-standing weakness which results from a patellofemoral problem, especially when that complicates the pain. The person in this circumstance is then in a double bind. They cannot use the knee for active daily living because it is weak, and they cannot do exercises to strengthen the knee because it is painful.

The concept behind the present invention is the separation of motion from pain so that effective exercise can be accomplished. In the example discussed immediately above, exercise is performed with the knee at rest, taking advantage of the knowledge that an isometric exercise performed at a series of different degrees of flexion will result in effective strength improvement throughout the entire range. This basic concept is applicable to other joints as well, including but not limited to the ankle and elbow.

In order to gain a fuller understanding of the problem and the proposed solution, we will continue with a discussion of a patient who has sustained an injury to the anterior cruciate ligament of his or her knee. A specific twisting mechanism ruptures a ligament within the knee; some bleeding and pain result. Common treatment for this injury is to immobilize the entire knee in an attempt to protect the knee from (1) further ligament injury; and (2) the pain and disability which result from the secondary swelling and fluid collection. However, total knee immobilization will result in deterioration or disuse changes in the muscles, connective tissues and surrounding bone. Strictly speaking, immobilization of the knee is unnecessary so long as the ligament is not further damaged. Therefore, what is really necessary is to maintain control of the knee while it is being exercised. It is for this reason the present proposal is advanced.

A further example is illustrated by a six-year old child with a long oblique fracture of the distal tibia. This fracture must be immobilized and protected from weight bearing. However, because of the nature of a child, simple instructions to avoid bearing weight on the leg, can go unheeded, thereby resulting in possible deformity and disability. A device to remind the child that such stresses are not allowed would be very helpful. If the present invention is provided with a load cell to sense such a load, a signal from a control device interconnected with the load cell could be programmed to alert the patient and/or the physician that inappropriate stress has been placed on the leg. Data from the load cell can also be recorded. The device 2 shown in FIG. 1 includes such a load cell 13 which can have the specific characteristics of any of the commonly available commercial load cells.

Another example would be an isolated medial collateral ligament tear of the knee. This is inherently a stable injury when appropriately protected. Some motion would be allowed and some muscle contraction would be allowed. However, at this time, no method is known to both support the extremity and provide the patient and doctor with enough feedback to allow cautious, protected strengthening and motion exercises to proceed.

An additional example would be an upper tibial fracture or osteotomy. If this were of the stable type, it would be surrounded by healthy tissues and healthy muscles at the outset of the injury or surgery, and motion and strengthening exercises could be allowed. What is currently keeping a patient from doing such motion and strengthening exercises is the lack of a sophisticated device to both maintain position and monitor strengthening exercises.

An upper tibial fracture theoretically could be formed in several ways. It could open like a book, it could be distracted, or it could rotate one fragment upon the other. Current treatment for this injury is to immobilize the extremity in a cast. This prevents translation and rotation, and the normal muscle contraction prevents distraction of the injury.

The ankle is a similar situation. The mortise of the ankle is actually a stable configuration. There is a buttress medially and laterally, and there is a curved surface into which the talar dome fits snugly. A person who inverts or rolls on the ankle may tear the ligaments on either side but normal muscle tension prevents translation of the talus. This is because the talus sits within these conforming structures. Treatment for such an injury is to immobilize the entire extremity in a cast. This results in atrophy of the calf muscles, atrophy of the surrounding bone, weakness and probably some slower healing of the injured ligaments. Clearly such strict immobilization is not necessary and probably is detrimental. It would be much preferable if such an injured ankle could be placed in a device which would both support the injury, encourage cautious protective motion or strength and finally monitor the degree of motion or strength as it occurs and any gains which may result from exercise.

It is known that bone should be exercised. It is believed that weight bearing applied to certain healing fractures may cause the fractures to heal faster and more predictably than if the fracture is not stressed at all. Similar responses are also believes to be expectable for connective tissues such as ligaments and articular cartilage.

Following his or her evaluation of an injury or disability, the doctor or prescribing professional makes a determination as to whether or not exercise will be allowed. Exercise is allowed when it is known that the injured tissue is stable and that exercise can be performed in a controlled manner. The problem which arises is that the physician or prescribing professional does not have adequate data to be assured that proper control can be maintained. The amount of force the patient can exert voluntarily is unknown and mechanisms for monitoring the exertion of force have, heretofore, been inadequate or nonexistent.

There are also injuries which are unstable. The cast applied to an unstable fracture cannot always protect it from deformity and collapse. Comminuted fractures of the tibia are an example of this. Such a proposed device would not apply to comminuted fracture of the tibia or similar injury unless it would be to surrounding structures which could safely be moved or exercised. The converse of such a device may be useful in that it would detect unwanted strains or stresses placed upon a potentially unstable injury reminding the patient and protecting from deformity which might otherwise occur.

The simplest and crudest method of protecting an injury at this time is the cast. This allows no movement, it allows no strengthening and it provides no data to the physician or patient. The cast is used when motion is not allowed, it is true that motion is most physiological for connective tissues but it is not always possible when control of the healing injury is necessary. Casts are associated with what is called cast or fracture disease. This is weakness of the muscles, atrophy of the muscles and bond and stiffness of the related joints. Some of these problems may be permanent. Other problems with cast immobilization include a possibility of developing phlebitis (the formation of blood clots), pressure sores or skin pressure changes. The resulting atrophy of connective tissue muscle or bone proximate the joint or injury, further results in weakness and/or stiffness of the joint and, finally, pain. It is not comfortable to have an extremity unnecessarily immobilized in a brace.

The next simple step in the mobilization of injuries has been to add a hinge to a cast. This does allow movement but it does not allow the patient to perform any strengthening and again is has not provided the patient or physician with any data. It would therefore be helpful if a cast brace could be instrumented in such a way that stresses within the brace could be monitored. It has always been a problem that the patient could not make the distinction between exercising the extremity without motion but still derive the benefits of exercise as if it had been performed with motion. The joint can be moved carefully but it cannot be moved forcefully.

Another example would be the debility and pain which follows a meniscus tear. The meniscus normally is a wedge-shaped structure which sits within the knee. It moves out of the way with flexion and extension of the knee. This, however, cannot occur if there is a tearing of the meniscus or some other type of joint damage. This tear of the meniscus results in pain, mechanical blockage or possibly retearing and further injury. therefore, when the patient attempts to rotate the femur against the tibia, the tear in the meniscus results in abnormal joint stresses and possible further injury. The same problem exists following repair of such a torn meniscus. The patient attempting to move the knee under unprotected and unmonitored conditions may redisplace the sutured meniscus tear. On the other hand, the knee may be able to bear the weight of certain types of exercise without motion or it may be able to bear the motion of certain types of exercise without weight or compressive force even though, it cannot bear the compressive forces and the motion together. There are two components of exercise, compressive force and motion. The present motion would assist the patient to separate these two components.

An additional problem exists within the failure of longitudinal structures. A patellar tendon, for example, if it is disrupted, is not adequately protected by surrounding the leg with a cast. It is a common problem in patellar tendon disruptions (or quadriceps disruptions or similar injuries) that the patient will attempt to move the extremity with a contraction of the associated muscle even though the tendon is damaged. This can result in further damage or can result in disruption of an attempted repair. At this time, it is simply suggested to the patient and they are reminded that they should not attempt to elevate the extremity. However, this is often not adequate. Normal reflex mechanisms cause the quadriceps muscle (in this case) to contract with hundreds of pounds of force which can cause these casted repairs to disrupt in the cast. For this reason, they, a device is necessary which could remind the patient that the extremity is being stressed in an impermissible way. It needs voluntary protection but it can only get that protection if the patient understands and is reminded in some way that the stresses are occurring.

An additional problem is that which results from the collection of blood within an immobilized extremity. Blood clots result and sometimes embolize to the lungs, creating serious medical problems. It would be of benefit to the patient if some type of reminding device could be placed in the cast or adjacent to the cast so that they could be reminded to exercise the calf muscle (in this case) pumping the blood, maintaining flow and preventing some of these serious medical problems. This could be done with certain types of stable injuries.

Oftentimes, the patients simply forget to do the exercises which are considered important. Patients are distracted by their activities of daily living and it is simply possible to forget about the extremity within the immobilization. When it is determined that exercise within protection is necessary, it would be most effective if the patient was both reminded by the protecting device and monitored as they execute the necessary activity.

It is known that patients who have fracture of the distal radius, adjacent to the wrist, may have long-term stiffness resulting from the immobilization of the fracture itself. In other words, if a patient has a wrist fracture and a cast only goes to the wrist leaving the fingers exposed, because of swelling which results from the injury, because of the pain which prevents active use, because of the forgetfulness of the patient and possibly because of the ignorance of the patient in understanding how important most exercises are: permanent stiffness can result. The fracture of the distal radius is particularly common in elderly patients who have osteoporosis. These elderly patients commonly have degenerative changes of the adjacent finger joints and the failure to move these joints during a period of protection (even when the fingers are not immobilized) results in permanent stiffness.

It is possible to use the present device 2 or 2" with the same cast or the same brace and the same treatment plan, but to obtain better compliance with the physician's instructions and better monitoring of the physician's instructions and better monitoring of the physician's instructions. In addition, such a device will provide documentation of the patient's response and cooperation.

Current casting methods are not simple. It is a complex process which is an art practiced by experts in the art. A cast must be strong, must fit properly, must hold securely and it must not cause any local problems such as allergic reaction and pressure sores. The physician's treatment plan would not have to change much at all. The physician could apply the same type of dressing but with the present device 2, monitor the patient's progress.

In summary, the physician would determine when stress can safely occur. This would be allowed when the injury is stable, when pain is controlled, and if the stress and motion to the area are controlled. Under these conditions, the doctor or medical professional would almost certainly conclude that stress to the tissues can occur safely and should be permitted. Controlled stress to injured tissue has been shown to result in facilitation of healing, less muscle atrophy, and the prevention of scar tissue with maintenance of normal, healthy connective tissue. Current methods have often failed. Rehabilitation is often forgotten while a patient is in a cast. The cast immobilizes the patient unnecessarily, resulting in atrophy, tissue damage, debility and stiffness.

The simplest solution to address these problems would be to provide a cast with elongated restraining bars, a strain gauge and some type of recording device. The device 2 would include a strain gauge 8 interconnected to an electronic monitoring or control unit 10. The electronic monitoring or control unit 10 would preferably allow the patient and the physician or therapist to monitor the following:

1. Maximum stress exerted.
2. The quality and duration of contraction.
3. The improvement of the person's strength over time.
4. Any unwanted movement (if flexion was occurring when only extension was desired or when translation of the bone was occurring when protection from translation was desired).

Strain gauges function through monitoring the electrical resistance of the tiny circuit. The kit could be applied in such a fashion to a cast that minute deformation of the cast could be monitored. These minute deformation which occur in even otherwise apparently rigid structures could be calibrated so that a person attempting to perform knee extension exercise to strengthen the quadriceps muscle could do so reliably either maximizing the contraction in the case of a stable injury or protecting from an excessive contraction in the case of a less stable injury. Again, the physician would be able to decide whether or not the injury is stable but now the physician has more adequate control because he has more useful data. The ideal device 2, therefore, would provide the information necessary for control as well as encouraging the exercise to occur, perhaps through some type of reminding device. The instrumented cast device 2, therefore, would result in better patient compliance, less debility and an overall smoother course of rehabilitation and healing.

As has been mentioned above, the simplest device 2 would be an instrumented cast. This would allow the patient to perform an isometric contraction at a fixed degree of flexion when it is determined that motion cannot be allowed. A second device 21 would allow the patient to vary the flexion points at which exercise is performed. It is believed that this would be desirable given the research findings presented below which are generally attributable to the literature cited:

"The isometric exercise performed at an angle of 15 degrees of knee flexion resulted in the average increase of 32 percent of the torque obtained at the corresponding test position (0.01)," Lindh, M., 1979, *Scandinavian Journal of Rehabilitation Medicine*, Vol . 11:33–36.

"Exercise performed at 60 degrees did not significantly increase the strength of the 15 degree angle." Lindh, M., 1979, *Scandinavian Journal of Rehabilitation Medicine,* 11:33–36.

It is believed that the ideal immobilization would be some type of adjustable and conforming brace which could be set to allow either no movement or only some certain movement. Such braces tend to be more comfortable than casts, more compliant, and with optimum design, should permit the same type of immobilization as obtained with a cast. The cast does not have the same advantage, however, because it cannot be modified to allow motion.

Other researchers who have studied related problems report the following findings:

There is a "position-dependent" effective isometric exercise. In other words, a patient who contracts the muscle in a fixed position will get strengthening at that position and at nearby flexion points. (These findings mainly agree with those of other authors who suggest that position-dependent isometric exercise is effective.) (Lindh, M., 1979, *Scandinavian Journal of Rehabilitation Medicine*, Vol. 11:33–36.

"Even a maximal static contraction voluntarily initiated is visualized as a neuromotor coordination capable of being influenced by motivation and a variety of other factors." Henry and Whitley, *The Research Quarterly*, vol. 31 (1)24–33.

Isometric exercise improves dynamic strength at a low velocity but not at a high velocity, Lindh, M., 1979, *Scandinavian Journal of Rehabilitation Medicine, Vol.* 11:33–36.

"It is consistent with the hypothesis that strength in action is controlled by neuromotor coordination centers of the nervous system and, hence, should exhibit the same high degree of specificity that is found in other types of neuromotor performances." Henry and Whitley, *The Research Quarterly*, Vol. 31 (1):24–33.

"The bulk of the evidence indicated that substantial strength gains could be obtained by the practice of isometric exercises of short duration." P. J. Rasch. 1961, *Journal of the Association for Physical and Mental Rehabilitation*, Vol. 15:46.

It was suggested that the isometric exercise would preferably be performed at different knee angles to secure an optimum total in strength increase. Lindh, M., 1979, *Scandinavian Journal of Rehabilitation Medicine*, Vol. 11:33–36.

"There is no such thing as a purely isometric contraction." P. J. Rasch, 1961, *Journal of the Association for Physical and Mental Rehabilitation*, Vol. 15:46–50.

In view of these findings it is believed that: (1) a patient benefits in both neuromuscular coordination and in absolute strength gains if exercises are done; and (2) if the isometric exercises are performed in a controlled fashion, the patient can derive benefit from those exercises, optimally the isometric exercise should be done at various degrees of joint flexion so that strength can be gained throughout the entire arc of flexion. This is because of an overlap phenomenon. Exercises performed at 45 degrees also results in some improvement in strength at 30 degrees and 50 degrees, but probably not at points of flexion far beyond those where exercise is performed. This means that this proposed device, which would allow exercise throughout the entire range of motion (isometric, under control, monitored, with feedback to the patient and memory to the doctor) would benefit the patient by allowing them to perform exercises that they do not perform under current methods because of voluntary compliance problems, pain. lack of appropriate data which would allow inadequate monitoring and expense. Currently, patient's are sent to physical therapy for instruction and monitoring. It is quite conceivable that such a device could provide better feedback to the patient, closer monitoring, more control and care more consistent with the doctor's instructions at a lower expense than physical therapy.

The basic underlying nature of these exercises is that they are simple but because of lack of compliance, supervision and feedback, these exercises are not being done and the patient suffers both subjectively in the form of pain and weakness but also objectively in the loss of connective tissue structure and other changes, some of which may be permanent. Some of these problems are life-threatening, such as when a patient fails to perform calf muscle contracting exercises (allowing a blood clot to form which may travel to the lungs). Some are simply debilitating (such as the stiffness which results from elderly degenerative hand joints following immobilization for otherwise simple wrist fractures). Some are not externally visible, such as the bony atrophy, which follows prolonged periods of immobilization. Bone material which is lost in this way, is lost as a result of a form of osteoporosis and may never be replaced. Some of the difficulty will be in the form of pain. A joint which is unnecessarily immobilized is uncomfortable and regaining that motion following a period of immobilization adds more discomfort, all of which is needless. Some of these changes are macroscopic; the visible atrophy of the muscle is apparent even to the casual observer. This should be prevented if at all possible, but some of the changes are microscopic or biochemical such as the loss of bony calcium, or the loss of connective tissue matrix.

In summary, a variety of severe and profound changes follow the needless immobilization of extremities and this proposed series of devices is designed to assist the physician by both maintaining control and providing data which is not otherwise available. This will improve patient care.

There are some additional areas for consideration as the present invention is developed. Consider the following problems.

1. Fifty-year old female who has undergone lumbar fusion stabilized adequately by metal plates and screws in the spine is advised to perform exercises, theoretically 30 foot pounds of flexion extension and side-bending torque are admissible within the limits of the internal fixation. Patient is already resting in a brace but has become dependent on the brace. The patient has no concept of what 15 pounds of isometric contraction against the walls of the brace would be and there is at this time no simple way to explain that to them. An instrumented brace would allow them to perform exercises which are currently not being done. They could do this in a controlled fashion, minimizing pain, weakness and stiffness, speeding their recovery.

2. Twenty-five year old white female with degeneration of the back of her right kneecap. At this time the pain is significant but is not as limiting as the combination of pain and weakness. The weakness has occurred insidiously, slowly, because direct spinal reflex has resulted in quadriceps atrophy. Currently, this patient is placed on simple straight leg raising exercises which clearly are not adequate. They improve her quadricep strength but only near full extension and this strength improvement is not helpful when the patient's knee is flexed as it must be to step off a curb or to ascent or descend stairs. The patient cannot take advantage of the currently available methods of physical therapy strengthening including the use of a Cybex machine or variant because extension of the knee against resistance aggravates her patellar changes, causing additional pain. This patient needs to exercise the knee at various fixed points of flexion because the patella will not hurt as much if it simply compressed: it only hurts if it is compressed and translated with its injured surface.

3. Sixty-five year old white male with severe degenerative arthritis to the knee has such severe quadriceps atrophy that he cannot undergo the proposed knee reconstruction. He cannot be placed on any exercise machine because this hurts too much. Simple straight leg raising exercises will not provide him the comprehensive form of strength that he needs through the entire dynamic range. This patient clearly needs to be able to exercise his knee is a controlled fashion, taking advantage of the pain relief which an isometric exercise occurs but also benefiting from the control of a proposed device which would allow him to perform quadriceps contractions, monitored adequately, at various fixed points of flexion.

A more complex rehabilitation problem is suggested by an individual with an anterior cruciate reconstruction. Under a common method of rehabilitation, the patient is able to do resistance exercises and a narrow flexion arc between 45 degrees and 90 degrees. An adjustable device 2' or 2" would allow the patient to lock their knee at various points of flexion between 45 degrees and 90 degrees of motion for the desirable strength there. Such a device could also monitor the maximum output of torque so that it could be maintained at a level consistent with protection of the reconstruction. It could be kept with the patient at home or be incorporated in their regular post-operative dressing so that visits to the physical therapist are unnecessary. The device would remind the patient to do the exercise, lock the hinge at the desired and acceptable degrees of knee flexion (as determined by the treating physician) monitor the quadriceps and hamstring contractions as well as perform the more basic function of protecting the knee from other forms of stress.

In summary, the ideal form of treatment is to rest only the injured tissue and to rest it only as much as it needs to be rested. The ideal would include the concept that other tissues around the injured tissue can be and should be moved and exercised so that their function is restored as rapidly as possible.

The present invention will be further described in accord with the following Examples.

Augmenting Devices Proposed Methods of Use

Five-Year-Old With Long Oblique Fracture Of Distal Tibia Weight Bearing Disallowed A child with a long oblique fracture of the distal tibia is a special problem since the child will not or cannot obey a medical instruction to protect the tibia against unwanted weight bearing. Shortening or deformity can result. Such a fracture is ordinarily treated in a long leg cast but cannot prevent the child from placing unwanted weight on the extremity.

A weight bearing alarm mechanism comprising a standard commercial load cell interconnected with a control unit including an alarm device is incorporated into the restraining device with the load cell located on the bottom of the cast or perhaps across the ankle so that a child bearing weight on the bast would be personally notified by some type of audible or palpable signal. Additionally, digital memory in the control unit records the number of infractions which occur for later feedback to the physician. This may be useful information in determining methods of treatment (altering the cast or the child's mobility), degree of healing and relative stability (an undisplaced fracture after multiple infractions and, in fact, be proven to be stable).

The physician and the patient would benefit from the use of an alarm mechanism to monitor a cast in a child with a long oblique fracture of the tibia in the following way:

The compliance of the individual is monitored and direct evidence is available to the physician as to whether or not further changes in the treatment program are necessary and whether or not compliance with the plan is present.

Time Release Mechanism For Range Of Motion Control

A person who has undergone anterior cruciate reconstruction or other types of ligament surgery about the knee is allowed only a certain degree of movement immediately after the surgery. The amount of movement allowed at the knee is gradually increased until the patient is approaching near full extension and near full flexion at 6–12 weeks post surgery.

There has always been some confusion as to exactly how fast the patient may progress. There is not a lot of literature data to support exactly what degree of freedom will protect the repair. Most orthopedists doing this type of surgery do believe that active extension against resistance near full extension may disrupt the repair, so most surgeons do not allow this initially.

The proposed augmentation of the electromechanical hinge device includes a time release mechanism such that a computer control unit interconnected with the electromechanical hinge would, with its internal clock, allow 45 degrees–90 degrees of flexion, let's say, at one week; 35 degrees–90 degrees at two weeks; 25 degrees–90 degrees of flexion at three weeks; and so on until the patient gradually reaches full extension.

At the present time the patient with such a hinge must report to the doctor's office to have the hinges adjusted, and sometimes this results in rather marked limitation in a patient's ability to move the knee. For example, a patient may go from an allowable flexion arc of 45 degrees–90 degrees degrees to an allowable flexion arc of 15 degrees–90 degrees at two or three weeks. This sudden release of the knee from such constraints is uncomfortable and the patient is pushing against more stiffness than if the knee had been allowed to release gradually. This results in a certain degree of discomfort.

A person with a time release hinge would be benefited in the following way:

(1) An electromechanically hinged brace would be applied to the knee following ligament reconstruction surgery, with the physician's desired protocol for motion programmed into the control unit of the brace.

(2) The brace would allow the patient to move the knee in the desired flexion arc immediately after surgery. Alternately or preferably, the brace may be locked by the time mechanism initially so that the patient may comfort during the early post-operative period when pain is most acute.

(3) The patient would be discharged from the hospital and the knee motion would be gradually regained at the expected rate by the surgeon's instructions as it is programmed into the brace. The patient may then be able to maintain contact with the physician over the phone, discussing how the motion is progressing within the brace, having direct digital readout and feedback through the computerized device.

(4) The patient would have, at the end of the period of immobilization, a more limber knee, a more efficient period of immobilization.

(5) The patient would probably have less discomfort since the allowable motion is returned to the knee gradually.

During the course of immobilization in the incrementally adjustable hinge, whether or not controlled by the timing mechanism, the patient may be able to lock their knee at various degrees of flexion, perhaps at 15 degree intervals, so that they can perform isometric contraction, gaining strength within the allowable flexion arc. This would be an application of the incrementally adjustable hinge concept within the electromechanical hinge concept. A combination of the incrementally adjustable hinge concept, the electromechanical hinge concept and the timing mechanism concept would be greatly advantageous to such a patient. Their pursuit of strength and motion would be optimized within the constraints of the needed immobilization and protection.

Instrumented Brace Proposed Method of Use

A Strengthening Device For A Torso To Be Used With Low Back, Upper Back Or Abdominal Muscular Weakness A person who has low back weakness is often asked to exercise the abdominal and spinal musculature to provide coordination and stabilizing effects on the spine. Many patients find this difficult because of the attendant pain which may be present in the presence of a compression fracture, degenerative disc disease, spinal arthritis or general debility following an injury.

A person would apply a brace to himself which would restrict motion in forward flexion and side bending, and the brace would be instrumented with strain gauges along its members, such that a person attempting to flex at the waist, for example, would be restrained from doing so (to prevent the motion which is often painful), but the strength in attempts at flexion could be monitored to document the degree of effort exhibited and the compliance over time. For example, a patient would apply the brace in an attempt to perform 15 flexion exercises at the waist, 15 extension exercises (where they attempt to lift the chest, let's say, off of the bed in a prone position), 15 side bending exercises to the left and 15 side bending exercises to the right. They would be reminded to execute the protocol, possibly by an alarm mechanism on the brace (if the brace were to be worn full-time), or by some other type of reminding device (if the brace was not indicated for continued wear). This would depend upon the patient's specific need and determination by the surgeon.

A person using such a device would benefit in the following ways:

(1) They would be able to safely and reliably use the device.

(2) They would be able to safely and reliably exercise their back in a protected fashion, even when no motion is allowed. This may allow certain individuals otherwise unable to exercise to do so in a controlled fashion. Isometric exercise, though perhaps not as beneficial as certain types of isotonic or dynamic resistance exercise, is preferable over no exercise at all.

(3) The patient's progress in strength, endurance and compliance could be monitored. The absolute strength could be monitored by the strain gauge, their endurance could be monitored by their ability to hold a forceful contraction over time. Their compliance could be monitored by measuring actual number of repetitions, number of days continued exercises, etc.

In summary, then, a patient using such an isometric conditioning device for the torso should be able to benefit by improvement in both strength and motion. The physician should be able to benefit by obtaining useful monitoring of the patient's improvement as it affects both objective and subjective parameters.

It is to be understood that even though numerous characteristics and advantages of various embodiments of the present invention have been set forth in the foregoing description, together with details of the structure and function of various embodiments of the invention, this disclosure is illustrative only, and changes may be made in detail, especially in matters of shape, size and arrangement of parts within the principles of the present invention to the full extent indicated by the broad general meaning of the terms in which the appended claims are expressed.

What is claimed is:

1. A communication unit comprising:
   (a) data input means for receiving an orthopedic parameters signal representative of a sensed stress in a personal orthopedic restraining device, the restraining device restraining movement of a first flexibly connected body portion relative to a second flexibly connected body portion of an individual;

(b) encoding means, operatively coupled to the data input means, for protecting the received orthopedic parameters signal from potential transmission errors by encoding the received orthopedic parameters signal;

(c) modulating means, operatively coupled to the encoding means, for preparing the encoded orthopedic parameters signal for subsequent transmission by modulating the encoded orthopedic parameters signal; and (d) transmitting means, operatively coupled to the modulating means, for transmitting the modulated orthopedic parameters signal over a communication channel such that movement of flexibly connected body portions can be monitored by a central site monitoring station; and further, wherein the orthopedic restraining device generates a message from the individual wearing the orthopedic restraining device, which is incorporated into the orthopedic parameters signal for transmission to the central monitoring station.

2. The communication unit of claim 1 wherein the encoding means comprises means for encoding the received orthopedic parameters signal according to an algorithm selected from the group consisting of: interleaving, block coding, convolutional coding, and cyclical redundant coding.

3. The communication unit of claim 1 wherein the modulating means comprises means for modulating the encoded orthopedic parameters signal according to a communication access type selected from the group consisting of: frequency division multiple access, time division multiple access, and code division multiple access.

4. The communication unit of claim 1 wherein the communication channel is selected from the group consisting of an electronic data bus, radio communication link, wireline, optical fiber link, and satellite link.

5. The communication unit of claim 1 wherein the transmitting means comprises means for transmitting the modulated orthopedic parameters signal over a communication channel of a type selected from the group consisting of a serial port wireline, a parallel port wireline, a public switched telephone network (PSTN), a private data network, a radio data network, a paging channel, a short message service channel, a personal communications service channel, a trunked radio channel, a cellular radio channel, and a satellite link.

6. The communication unit of claim 1 further comprising a detachable connection mechanism for selectively connecting the communication unit to the personal orthopedic restraining device.

7. The communication unit of claim 1 further comprising a power supply detachably connected to the personal orthopedic restraining device and the communication unit, the power supply being shaped and arranged for optimal positioning on the individual which will be wearing the personal orthopedic restraining device and the communication unit.

8. The communication unit of claim 7 wherein the power supply is a rechargeable battery.

9. The communication unit of claim 1 wherein the orthopedic parameters signal comprises a sensed stress value representative of a total torque output by the individual over a period of time as measured by the personal orthopedic restraining device.

10. The communication unit of claim 9 wherein the orthopedic parameters signal further comprises a patient identifier.

11. The communication unit of claim 9 wherein the data input means comprises means for incorporating messages obtained from the individual into the orthopedic parameters signal for transmission to the central site monitoring station.

12. The communication unit of claim 1 further comprising a receiving means for receiving a communication from the central site monitoring station over the communication channel.

13. The communication unit of claim 12 wherein the central site monitoring station communication is selected from the group consisting of: a message to the individual wearing the personal orthopedic restraining device and the communication unit, a programming instruction for the personal orthopedic restraining device, a request for an orthopedic parameter signal from the personal orthopedic restraining device, a request to resend a portion of an orthopedic parameter signal previously sent by the personal orthopedic restraining device, and confirmation that a previous orthopedic parameter signal was received.

14. The communication unit of claim 13 further comprising data output means for providing the central site monitoring station communication to the personal orthopedic restraining device.

15. A central site monitoring station communication unit comprising:

(a) receiving means for receiving a modulated orthopedic parameters signal from a personal orthopedic restraining device worn by an individual, the modulated orthopedic parameters signal being representative of a sensed stress in the restraining device;

(b) demodulating means, operatively coupled to the receiving means, for demodulating the received modulated orthopedic parameters signal;

(c) detecting means, operatively coupled to the demodulating means, for detecting an orthopedic parameters signal from demodulated orthopedic parameters signal; and (d) data output means, operatively coupled to the detecting means, for providing the detected orthopedic parameters signal to an external device such that subsequent processing of the orthopedic parameters signal can be performed; and further, wherein the orthopedic restraining device generates a message from the individual wearing the orthopedic restraining device, which is incorporated into the orthopedic parameters signal for transmission to the central monitoring station.

16. The central site monitoring station communication unit of claim 15 wherein the communication channel is selected from the group consisting of an electronic data bus, radio communication link, wireline, optical fiber link, and satellite link.

17. The central site monitoring station communication unit of claim 15 wherein the receiving means comprises means for receiving the modulated orthopedic parameters signal from a communication channel of a type selected from the group consisting of a serial port wireline, a parallel port wireline, a public switched telephone network (PSTN), a private data network, a radio data network, a paging channel, a short message service channel, a personal communications service channel, a trunked radio channel, a cellular radio channel, and a satellite link.

18. The central site monitoring station communication unit of claim 15 wherein the demodulating means comprises means for demodulating the received modulated orthopedic parameters signal based on the received modulated orthopedic parameters signal having a communication access type selected from the group consisting of: frequency division multiple access, time division multiple access, and code division multiple access.

19. The central site monitoring station communication unit of claim 15 wherein the detecting means comprises means for detecting transmission errors in the demodulated orthopedic parameters signal.

20. The central site monitoring station communication unit of claim 15 wherein the detecting means comprises means for correcting transmission errors in the demodulated orthopedic parameters signal based on a maximum likelihood sequence estimation algorithm.

21. The central site monitoring station communication unit of claim 15 further comprising transmitting means for transmitting a communication from the central site monitoring station over the communication channel to the personal orthopedic restraining device.

22. The central site monitoring station communication unit of claim 21 wherein the central site monitoring station communication is selected from the group consisting of: a message to the individual wearing the personal orthopedic restraining device and the communication unit, a programming instruction for the personal orthopedic restraining device, a request for an orthopedic parameter signal from the personal orthopedic restraining device, a request to resend a portion of an orthopedic parameter signal previously sent by the personal orthopedic restraining device, and confirmation that a previous orthopedic parameter signal was received.

23. The central site monitoring station communication unit of claim 15 further comprising the external device, the external device comprising means for performing subsequent processing of the orthopedic parameters signal, the orthopedic parameters signal comprising a sensed stress value representative of a total torque output by the individual over a period of time as measured by the personal orthopedic restraining device.

24. The central site monitoring station communication unit of claim 23 wherein the subsequent processing is selected from the group consisting of: comparing the sensed stress value to an expected value to confirm that the individual's responses are within norms, comparing the sensed stress value to previously received values associated with a patient identifier for the individual to judge the individual's response to treatment, storing the sensed stress value along with previously received values associated with a patient identifier for the individual to create a clinical record, monitoring a prescribed exercise regimen of the individual based on the sensed stress value to monitor compliance with the prescribed exercise regimen, performing statistical analysis of the sensed stress value in conjunction with other values received at the central site monitoring station, providing a message obtained from the individual wearing the personal orthopedic device to another individual at the central site monitoring station, and determining a programming instruction to be sent to the personal orthopedic restraining device.

25. A remote communication unit comprising:
(a) a data input for receiving an orthopedic parameters signal, the orthopedic parameters signal at least including a value representative of a total torque output by an individual over a period of time as measured by a personal orthopedic restraining device, the restraining device restraining movement of a first flexibly connected body portion relative to a second flexibly connected body portion of an individual;
(b) an encoder, operatively coupled to the data input, for protecting the received orthopedic parameters signal from potential transmission errors by encoding the received orthopedic parameters signal;
(c) a modulator, operatively coupled to the encoder, for preparing the encoded orthopedic parameters signal for subsequent transmission by modulating the encoded orthopedic parameters signal;
(d) a transmitter, operatively coupled to the modulator, for transmitting the modulated orthopedic parameters signal over a communication channel such that movement of flexibly connected body portions can be monitored by a central site monitoring station;
(e) a receiver for receiving a communication from the central site monitoring station over the communication channel;
(f) a data output for providing the central site monitoring station communication to the personal orthopedic restraining device; and
(g) a detachable connection mechanism for selectively connecting the communication unit to the personal orthopedic restraining device; and further,
wherein the orthopedic restraining device generates a message from the individual wearing the orthopedic restraining device, which is incorporated into the orthopedic parameters signal for transmission to the central monitoring station.

26. The remote communication unit of claim 25 wherein the data input comprises a mechanism for incorporating messages obtained from the individual into the orthopedic parameters signal for transmission to the central site monitoring station.

27. The remote communication unit of claim 25 further comprising a power supply detachably connected to the personal orthopedic restraining device and to the communication unit, the power supply being shaped and arranged for optimal positioning on the individual which will be wearing the personal orthopedic restraining device and the communication unit.

28. The remote communication unit of claim 25 wherein the central site monitoring station communication is selected from the group consisting of: a message to the individual wearing the personal orthopedic restraining device and the communication unit, a programming instruction for the personal orthopedic restraining device, a request for an orthopedic parameter signal from the personal orthopedic restraining device, a request to resend a portion of an orthopedic parameter signal previously sent by the personal orthopedic restraining device, and confirmation that a previous orthopedic parameter signal was received.

29. A central site monitoring station communication unit comprising:
(a) receiver for receiving a modulated orthopedic parameters signal from a personal orthopedic restraining device worn by an individual, the modulated orthopedic parameters signal being representative of a sensed stress in the restraining device;
(b) demodulator, operatively coupled to the receiver, for demodulating the received modulated orthopedic parameters signal;
(c) detector, operatively coupled to the demodulator, for detecting an orthopedic parameters signal from demodulated orthopedic parameters signal, the detector including a transmission error detector for detecting errors in the demodulated orthopedic parameters signal;
(d) a processor, operatively couple to the detector, for performing subsequent processing of the orthopedic parameters signal, the orthopedic parameters signal comprising a sensed stress value representative of a total torque output by the individual over a period of time as measured by the personal orthopedic device; and (e) a transmitter, operatively coupled to the processor, for transmitting a communication from the central site monitoring station over the communication channel to the personal orthopedic restraining device; and further, wherein the orthopedic restraining device generates a message from the individual wearing the orthopedic restraining device, which is incorporated into the orthopedic parameters signal for transmission to the central monitoring station.

30. The central site monitoring station communication unit of claim 29 wherein the detector comprises a mechanism for correcting transmission errors in the demodulated orthopedic parameters signal based on a maximum likelihood sequence estimation algorithm.

31. The central site monitoring station communication unit of claim 29 wherein the central site monitoring station communication is selected from the group consisting of: a message to the individual wearing the personal orthopedic restraining device and the communication unit, a programming instruction for the personal orthopedic restraining device, a request for an orthopedic parameter signal from the personal orthopedic restraining device, a request to resend a portion of an orthopedic parameter signal previously sent by the personal orthopedic restraining device, and confirmation that a previous orthopedic parameter signal was received.

32. The central site monitoring station communication unit of claim 29 wherein the subsequent processing is selected from the group consisting of: comparing the sensed stress value to an expected value to confirm that the individual's responses are within norms, comparing the sensed stress value to previously received values associated with a patient identifier for the individual to judge the individual's response to treatment, storing the sensed stress value along with previously received values associated with a patient identifier for the individual to create a clinical record, monitoring a prescribed exercise regimen of the individual based on the sensed stress value to monitor compliance with the prescribed exercise regimen, performing statistical analysis of the sensed stress value in conjunction with other values received at the central site monitoring station, providing a message obtained from the individual wearing the personal orthopedic device to another individual at the central site monitoring station, and determining a programming instruction to be sent to the personal orthopedic restraining device.

33. A personal orthopedic restraining device for use to restrain flexibly connected body portions of an individual, the personal orthopedic restraining device comprising:

(a) restraining means for restraining movement of a first flexibly connected body portion relative to a second flexibly connected body portion;

(b) stress sensing means, operatively attached to the restraining means, for providing an output signal representative of a sensed stress in the restraining means;

(c) memory storage device;

(d) output port means for communicating a routine result from the memory storage device to a remote device external to the personal orthopedic restraining device; and (e) control means, operatively coupled to the stress sensing means, the memory storage device, and the output port means, for processing to stress sensing means output signal according to a previously programmed routine to obtain a routine result and to communicate the routine result to the remote device, the control means storing the routine result in the memory storage device such that the routine result can be used by the personal orthopedic restraining device to monitor movement of flexibly connected body portions; and further, wherein the orthopedic restraining device generates a message from the individual wearing the orthopedic restraining device, which is incorporate into the orthopedic parameter signal for transmission to the central monitoring station.

34. The personal orthopedic restraining device of claim 33 wherein the output port means comprises input means for communicating information from the remote device to the memory storage device, and wherein the previously programmed routine further comprises communicating information from the remote device to the memory storage device.

35. The personal orthopedic restraining device of claim 33 wherein the remote device is selected from the group consisting of:

(d)(i) a printer which generates a printout on the printer based on the routine result information stored in the memory storage device;

(d)(ii) an external storage device which receives the routine result information from the memory storage device such that transfer of the routine result to a remote location is provided;

(d)(iii) a wireless transmitter for transmitting the routine result information stored in the memory storage device to the remote device such that the routine result can be transmitted to a remote host;

(d)(iv) a wireline modem for transmitting the routine result information stored in the memory storage device to the remote device such that the routine result can be transmitted to a remote host; and (d)(v) a direct wireline connection to the remote device for transmitting the routine result information stored in the memory storage device to the remote device such that the routine result can be transmitted to a remote host.

36. A method of communicating an orthopedic parameters signal between a remote communication unit and a central site monitoring station, the orthopedic parameters signal at least including a value representative of a total torque output by an individual over a period of time as measured by a personal orthopedic restraining device, the restraining device restraining movement of a first flexibly connected body portion relative to a second flexibly connected body portion of an individual, the method comprising the steps of:

(a) receiving the orthopedic parameters signal at the remote communication unit from the personal orthopedic restraining device;

(b) protecting the received orthopedic parameters signal from potential transmission errors by encoding the received orthopedic parameters signal;

(c) preparing the encoded orthopedic parameters signal for subsequent transmission by modulating the encoded orthopedic parameters signal; and (d) transmitting the modulated orthopedic parameters signal over a communication channel from the remote communication unit and to the central site monitoring station such that movement of flexibly connected body portions can be monitored by the central site monitoring station; and further, wherein the orthopedic restraining device generates a message from the individual wearing the orthopedic restraining device, which is incorporated into the orthopedic parameters signal for transmission to the central monitoring station.

37. The method of claim 36 wherein the encoding step comprises encoding the received orthopedic parameters signal according to an algorithm selected from the group consisting of: interleaving, block coding, convolutional coding, and cyclical redundant coding.

38. The method of claim 36 wherein the modulating step comprises modulating the encoded orthopedic parameters signal according to a communication access type selected from the group consisting of: frequency division multiple access, time division multiple access, and code division multiple access.

39. The method of claim 36 wherein the transmitting step comprises preparing the modulated orthopedic parameters signal for transmission over a particular type of communication channel selected from the group consisting of a serial port wireline, a parallel port wireline, a public switched telephone network (PSTN), a private data network, a radio data network, a paging channel, a short message service channel, a personal communications service channel, a trunked radio channel, a cellular radio channel, and a satellite link.

40. The method of claim 36 further comprising the step of connecting the remote communication unit to the personal orthopedic restraining device prior to performing the receiving step.

41. The method of claim 36 further comprising the step of connecting the remote communication unit to a communication channel coupler prior to performing the transmitting step, the communication channel coupler being configured for use with a particular type of communication channel selected from the group consisting of an electronic data bus, radio communication link, wireline, optical fiber link, and satellite link.

42. The method of claim 36 further comprising the step of storing at least two different orthopedic parameters signals and wherein the transmitting step comprises transmitting modulated versions of the stored at least two orthopedic parameters signals in a single transmission burst over the communication channel.

43. The method of claim 36 wherein the method comprises a one-way communication scheme.

44. The method of claim 43 wherein the receiving step comprises receiving the orthopedic parameters signal after an action has occurred selected from the group consisting of: a prescribed exercise regimen has been completed, a periodic reporting time has occurred, at least two different orthopedic parameters signals have been generated by the personal orthopedic device, and a message has been obtained from the individual for incorporation into the orthopedic parameters signal for transmission to the central site monitoring station.

45. The method of claim 36 further comprising a step of receiving a communication from the central site monitoring station over the communication channel such that the method comprises a two-way communication scheme.

46. The method of claim 45 wherein the receiving step comprises receiving the orthopedic parameters signal after an action has occurred selected from the group consisting of: a prescribed exercise regimen has been completed, a periodic reporting time has occurred, at least two different orthopedic parameters signals have been generated by the personal orthopedic device, a message has been obtained from the individual for incorporation into the orthopedic parameters signal for transmission to the central site monitoring station, and a communication has been received from the central site monitoring station which requests an orthopedic parameter signal from the personal orthopedic restraining device.

47. The method of claim 45 further comprising a step of providing the central site monitoring station communication to the personal orthopedic restraining device.

48. The method of claim 45 wherein the receiving step comprises receiving a limited-short communication over a limited communication channel selected from the group consisting of a radio data network, a paging channel, a short message service channel, a personal communications service channel, a trunked radio channel, a cellular radio channel, and a satellite link and wherein the limited-short communication is selected from the group consisting of: a request for an orthopedic parameter signal from the personal orthopedic restraining device, a request to resend a portion of an orthopedic parameter signal previously sent by the personal orthopedic restraining device, and confirmation that a previous orthopedic parameter signal was received.

49. The method of claim 45 wherein the receiving step comprises receiving a full-long communication over a full communication channel selected from the group consisting of a radio data network, a paging channel, a short message service channel, a personal communications service channel, a trunked radio channel, a cellular radio channel, and a satellite link and wherein the full-long communication is selected from the group consisting of: a message to the individual wearing the personal orthopedic restraining device and the communication unit, a programming instruction for the personal orthopedic restraining device, a request for an orthopedic parameter signal from the personal orthopedic restraining device, a request to resend a portion of an orthopedic parameter signal previously sent by the personal orthopedic restraining device, and confirmation that a previous orthopedic parameter signal was received.

50. A method of communicating an orthopedic parameters signal between a remote communication unit and a central site monitoring station, the orthopedic parameters signal at least including a value representative of a total torque output by an individual over a period of time as measured by a personal orthopedic restraining device, the restraining device restraining movement of a first flexibly connected body portion relative to a second flexibly connected body portion of an individual, the method comprising the steps of:

(a) receiving a modulated version of the orthopedic parameters signal at the central site monitoring station;

(b) demodulating the received modulated orthopedic parameters signal;

(c) detecting an orthopedic parameters signal from demodulated orthopedic parameters signal; and (d) providing the detected orthopedic parameters signal to an external device such that subsequent processing of the orthopedic parameters signal can be performed; and further, wherein the orthopedic restraining device generates a message from the individual wearing the orthopedic restraining device, which is incorporated into the orthopedic parameters signal for transmission to the central monitoring station.

51. The method of claim 50 further comprising the step of connecting the central site monitoring station to a communication channel coupler prior to performing the receiving step, the communication channel coupler being configured for use with a particular type of communication channel selected from the group consisting of an electronic data bus, radio communication link, wireline, optical fiber link, and satellite link.

52. The method of claim 50 wherein the receiving step comprises receiving the modulated version of the orthopedic parameters signal from a particular type of communication channel selected from the group consisting of a serial port wireline, a parallel port wireline, a public switched telephone network (PSTN), a private data network, a radio data network, a paging channel, a short message service channel, a personal communications service channel, a trunked radio channel, a cellular radio channel, and a satellite link.

53. The method of claim 50 wherein the demodulating step comprises demodulating the received modulated orthopedic parameters signal based on the received modulated orthopedic parameters signal having a communication access type selected from the group consisting of: frequency division multiple access, time division multiple access, and code division multiple access.

54. The method of claim 50 wherein the detecting step comprises detecting transmission errors in the demodulated orthopedic parameters signal.

55. The method of claim 50 wherein the detecting step comprises correcting transmission errors in the demodulated orthopedic parameters signal based on a maximum likelihood sequence estimation algorithm.

56. The method of claim 50 further comprising the step of transmitting a communication from the central site monitoring station over the communication channel to the personal orthopedic restraining device.

57. The method of claim 56 wherein the central site monitoring station communication is selected from the group consisting of: a message to the individual wearing the personal orthopedic restraining device and the communication unit, a programming instruction for the personal orthopedic restraining device, a request for an orthopedic parameter signal from the personal orthopedic restraining device, a request to resend a portion of an orthopedic parameter signal previously sent by the personal orthopedic restraining device, and confirmation that a previous orthopedic parameter signal was received.

58. The method of claim 56 further comprising the step of performing subsequent processing of the orthopedic parameters signal in the external device, the subsequent processing being selected from the group consisting of: comparing the sensed stress value to an expected value to confirm that the individual's responses are within norms, comparing the sensed stress value to previously received values associated with a patient identifier for the individual to judge the individual's response to treatment, storing the sensed stress value along with previously received values associated with a patient identifier for the individual to create a clinical record, monitoring a prescribed exercise regimen of the individual based on the sensed stress value to monitor compliance with the prescribed exercise regimen, performing statistical analysis of the sensed stress value in conjunction with other values received at the central site monitoring station, providing a message obtained from the individual wearing the personal orthopedic device to another individual at the central site monitoring station, and determining a programming instruction to be sent to the personal orthopedic restraining device.

59. A one-way method of communicating an orthopedic parameters signal between a remote communication unit and a central site monitoring station, the orthopedic parameters signal at least including a value representative of a total torque output by an individual over a period of time as measured by a personal orthopedic restraining device, the restraining device restraining movement of a first flexibly connected body portion relative to a second flexibly connected body portion of an individual, the method comprising the steps of:

(a) waiting for a particular action to occur selected from the group consisting of: completing a prescribed exercise regimen, happening of a periodic reporting time, generating at least two different orthopedic parameters signals by the personal orthopedic device, and obtaining a message from the individual for incorporation into the orthopedic parameters signal for transmission to the central site monitoring station;

(b) receiving, subsequent to the particular action occurring, the orthopedic parameters signal at the remote communication unit from the personal orthopedic restraining device;

(c) protecting the received orthopedic parameters signal from potential transmission errors by encoding the received orthopedic parameters signal;

(d) preparing the encoded orthopedic parameters signal for subsequent transmission by modulating the encoded orthopedic parameters signal;

(e) transmitting the modulated orthopedic parameters signal over a communication channel from the remote communication unit and to the central site monitoring station such that movement of flexibly connected body portions can be monitored by the central site monitoring station;

(f) receiving the modulated orthopedic parameters signal at the central site monitoring station from over the communication channel;

(g) demodulating the received modulated orthopedic parameters signal;

(h) detecting an orthopedic parameters signal from demodulated orthopedic parameters signal; and (i) providing the detected orthopedic parameters signal to an external device such that subsequent processing of the orthopedic parameters signal can be performed; and further, wherein the orthopedic restraining device generates a message from the individual wearing the orthopedic restraining device, which is incorporated into the orthopedic parameters signal for transmission to the central monitoring station.

60. A method of using a personal orthopedic restraining device which restrains flexibly connected body portions of an individual, the method comprising the steps of:

(a) providing an orthopedic restraining device, the orthopedic restraining device including: restraining means for restraining movement of a first flexibly connected body portion relative to as second flexibly connected body portion, stress sensing means, operatively attached to the restraining means, for providing an output signal representative of a sensed stress in the restraining means, memory storage device, output port means for communicating a routine result from the memory storage device to a remote device external to the personal orthopedic restraining device, and control means, operatively couple to the stress sensing means, the memory storage device, and the output port means, for processing the stress sensing means output signal according to a previously programmed routine to obtain a routine result, the control means storing the routine result in the memory storage device device; and (b) communicating the routine result from the memory storage device to the remote device via the output port such that analysis of the routine result can be conducted at a later time; and further wherein the orthopedic restraining device generates a message from the individual wearing the orthopedic restraining device, which is incorporated into the orthopedic parameters signal for transmission to the central monitoring station.

* * * * *